US007816490B2

(12) United States Patent
Hogan et al.

(10) Patent No.: US 7,816,490 B2
(45) Date of Patent: *Oct. 19, 2010

(54) SPECIFIC INHIBITORS OF NFAT ACTIVATION BY CALCINEURIN AND THEIR USE IN TREATING IMMUNE-RELATED DISEASES

(75) Inventors: Patrick G. Hogan, Cambridge, MA (US); Anjana Rao, Cambridge, MA (US); Jose Aramburu, Boston, MA (US)

(73) Assignee: Immune Disease Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/260,049

(22) Filed: Oct. 28, 2008

(65) Prior Publication Data

US 2009/0186422 A1    Jul. 23, 2009

Related U.S. Application Data

(60) Division of application No. 11/474,218, filed on Jun. 23, 2006, now abandoned, which is a continuation of application No. 10/066,151, filed on Jan. 31, 2002, now Pat. No. 7,084,241, which is a continuation of application No. 09/248,620, filed on Feb. 11, 1999, now abandoned.

(60) Provisional application No. 60/074,467, filed on Feb. 12, 1998.

(51) Int. Cl.
*C07K 7/00* (2006.01)
*C07K 7/06* (2006.01)
*C07K 7/08* (2006.01)
*C07K 14/00* (2006.01)

(52) U.S. Cl. ........................ 530/330; 530/324; 530/326; 530/328

(58) Field of Classification Search ........................ None
See application file for complete search history.

(56) References Cited

U.S. PATENT DOCUMENTS

| 5,612,455 | A | 3/1997 | Hoey |
| 5,656,452 | A | 8/1997 | Rao et al. |
| 5,708,158 | A | 1/1998 | Hoey |
| 5,837,840 | A | 11/1998 | Crabtree et al. |
| 5,863,738 | A * | 1/1999 | Dijke et al. ................ 435/7.1 |
| 5,872,218 | A * | 2/1999 | Wolf et al. ................ 530/387.9 |
| 6,096,515 | A | 8/2000 | Crabtree et al. |
| 6,150,099 | A | 11/2000 | Crabtree et al. |
| 6,171,781 | B1 | 1/2001 | Crabtree et al. |
| 6,197,925 | B1 | 3/2001 | Crabtree et al. |
| 6,352,830 | B1 | 3/2002 | Crabtree et al. |

FOREIGN PATENT DOCUMENTS

| WO | WO 93/22338 | 11/1993 |
| WO | WO 94/03205 | 2/1994 |
| WO | WO 94/18234 | 8/1994 |
| WO | WO 94/20127 | 9/1994 |
| WO | WO 96/26959 | 9/1996 |

OTHER PUBLICATIONS

Clipstone et al., "Identification of Calcineurin as a Key Signalling Enzyme in T-lymphocyte Activation", *Nature*, vol. 357:695-697 (1992).
Loh et al., "Calcineurin Binds the Transcription Factor NFAT1 and Reversibly Regulates Its Activity", *J. Biological Chemistry*, vol. 271:10884-10891 (1996).
Luo et al., "Interaction of Calcineurin With a Domain of the Transcription Factor NFAT1 that Controls nuclear Import", *Proc. Natl. Acad. Sci.*; vol. 93:8907-8912 (1996).
Masuda et al., "Control of NFATx1 Nuclear Translocation by a Calcineurin-Regulated Inhibitory Domain", *Molecular and Cellular Biology*, vol. 17:2066-2075 (1997).
Mickle et al., "Genotype-phenotype relationships in cystic fibrosis", *Med Clin North Am*, vol. 84:597-607 (2000).
Park et al., "Phosphorylation of the Transcription Factor NFATp Inhibits Its DNA Binding Activity in Cyclosporin A-treated Human B and T Cells", *J. Biological Chemistry*, vol. 270:20653-20659 (1995).
Rao, et al., "Transcription Factors of the NFAT Family: Regulation and Function", *Annual Reviews, Inc.*, vol. 15:707-747 (1997).
Ruff et al., "Direct demonstration of NFATp dephosphorylation and nuclear localization in activated HT-2 cells using a specific NFATp polyclonal antibody.", *J. Biological Chemistry*, vol. 270:22602-22607 (1995).
Shaw et al., "Immunosuppressive Drugs prevent a Rapid Dephosphorylation of Transcription Factor NFAT1 in Stimulated Immune Cells", *Cell Biology*, vol. 92:11205-11209 (1995).
Shibasaki et al., "Role of Kinases and the Phosphatase Calcineurin in the Nuclear Shuttling of Transcription Factor NF-AT4", *Nature*, vol. 382:370-373 (1996).
Timmerman et al., "Rapid shuttling of NF-AT in Discrimination of Ca2 signals and Immunosuppression", *Nature*, vol. 383:837-840 (1996).
Voet et al., Biochemistry, 1990, John Wiley & Sons, Inc. pp. 126-128 and 228-234.
Wesselborg et al., "Identification of a Physical Interaction between Calcineurin and Nuclear Factor of Activated T Cells (NFATp)", *J. Biological Chemistry*, vol. 271:1274-1277 (1996).
Yan et al., "Two-amino acid molecular switch in an epithelial morphogen that regulates binding to two distinct receptors", *Science*, vol. 290:523-527 (2000).

\* cited by examiner

*Primary Examiner*—Gary B. Nickol
*Assistant Examiner*—Elly-Gerald Stoica
(74) *Attorney, Agent, or Firm*—Fish & Richardson P.C.

(57) ABSTRACT

Isolated peptide fragments of the conserved regulatory domain of NFAT protein capable of inhibiting protein-protein interaction between calcineurin and NFAT, or a biologically active analog thereof are described. Isolated polynucleotides and gene therapy vectors encoding such peptide fragments are also described. In addition, methods for treating immune-related diseases or conditions and methods for high throughput screening of candidate agents are described. Pharmaceutical compositions are also provided.

18 Claims, 8 Drawing Sheets

Fig. 1

| | |
|---|---|
| $IX_2X_3T$ | (SEQ ID NO:104) |
| IEIT | (SEQ ID NO:105) |
| IRIT | (SEQ ID NO:106) |
| IQIT | (SEQ ID NO:107) |
| IQFT | (SEQ ID NO:108) |
| | |
| $X_1IX_2X_3T$ | (SEQ ID NO:73) |
| $X_1IX_2IT$ | (SEQ ID NO:74) |
| $RIX_2IT$ | (SEQ ID NO:75) |
| $X_1IEIT$ | (SEQ ID NO:76) |
| RIEIT | (SEQ ID NO:1) |
| SIRIT | (SEQ ID NO:2) |
| SIQIT | (SEQ ID NO:3) |
| SIQFT | (SEQ ID NO:4) |
| | |
| $PX_1IX_2X_3T$ | (SEQ ID NO:77) |
| PRIEIT | (SEQ ID NO:5) |
| PSIRIT | (SEQ ID NO:6) |
| PSIQIT | (SEQ ID NO:71) |
| PSIQFT | (SEQ ID NO:7) |
| | |
| $X_5PX_1IX_2X_3T$ | (SEQ ID NO:78) |
| SPRIEIT | (SEQ ID NO:8) |
| CPSIRIT | (SEQ ID NO:9) |
| CPSIQIT | (SEQ ID NO:10) |
| CPSIQFT | (SEQ ID NO:11) |

Fig. 1 (continued)

| | |
|---|---|
| $X_5PX_1IX_2X_3TX_6$ | (SEQ ID NO:79) |
| SPRIEITP | (SEQ ID NO:12) |
| SPRIEITS | (SEQ ID NO:13) |
| CPSIRITS | (SEQ ID NO:14) |
| CPSIQITS | (SEQ ID NO:15) |
| CPSIQFTS | (SEQ ID NO:16) |
| | |
| $X_5PX_1IX_2X_3TX_6X_7$ | (SEQ ID NO:80) |
| SPRIEITPS | (SEQ ID NO:17) |
| SPRIEITSC | (SEQ ID NO:18) |
| CPSIRITSI | (SEQ ID NO:19) |
| CPSIQITSI | (SEQ ID NO:20) |
| CPSIQFTSI | (SEQ ID NO:21) |
| SPAIAIAPS | (SEQ ID NO:82) |
| | |
| $X_{11}X_{10}X_9X_5PX_1IX_2X_3TX_6X_7X_8$ | (SEQ ID NO:81) |
| SGPSPRIEITPSH | (SEQ ID NO:22) |
| SGLSPRIEITPSH | (SEQ ID NO:23) |
| ALESPRIEITSCL | (SEQ ID NO:24) |
| VLECPSIRITSIS | (SEQ ID NO:25) |
| PFECPSIQITSIS | (SEQ ID NO:26) |
| PFECPSIQITSIS | (SEQ ID NO:27) |
| PFECPSIQFTSIS | (SEQ ID NO:28) |

Fig. 1 (continued)

| | | |
|---|---|---|
| KPAGASGPSPRIEITPSHELMQAGG | (SEQ ID NO:29) | murine NFAT1 |
| KPAGASGLSPRIEITPSHELIQAVG | (SEQ ID NO:30) | human NFAT1 |
| PDGAPALESPRIEITSCLGLYHNNN | (SEQ ID NO:31) | human NFAT2 |
| AGGGRVLECPSIRITSISPTPEPPA | (SEQ ID NO:32) | human NFAT3 |
| LGGPKPFECPSIQITSISPNCHQEL | (SEQ ID NO:33) | human NFAT4 |
| LGGPKPFECPSIQITSISPNCHQGT | (SEQ ID NO:34) | murine NFAT4 (Ho) |
| LGGPKPFECPSIQFTSISPNCQQEL | (SEQ ID NO:35) | murine NFAT4 (Liu) |

Fig. 2

ATCGAGATCACT (SEQ ID NO:110)
I   E   I   T

ATCGAGATAACC (SEQ ID NO:111)
I   E   I   T

ATCCGCATCACC (SEQ ID NO:112)
I   R   I   T

ATTCAAATTACA (SEQ ID NO:113)
I   Q   I   T

ATTCAAATCACA (SEQ ID NO:114)
I   Q   I   T

ATCCAATTTACA (SEQ ID NO:115)
I   Q   F   T

CGGATCGAGATCACT (SEQ ID NO:36)
R   I   E   I   T

CGCATCGAGATAACC (SEQ ID NO:83)
R   I   E   I   T

AGCATCCGCATCACC (SEQ ID NO:37)
S   I   R   I   T

AGTATTCAAATTACA (SEQ ID NO:38)
S   I   Q   I   T

AGTATTCAAATCACA (SEQ ID NO:84)
S   I   Q   I   T

AGTATCCAATTTACA (SEQ ID NO:39)
S   I   Q   F   T

Fig. 2 (continued)

```
CCTCGGATCGAGATCACT          (SEQ ID NO:40)
 P   R   I   E   I   T

CCTCGCATCGAGATAACC          (SEQ ID NO:85)
 P   R   I   E   I   T

CCCAGCATCCGCATCACC          (SEQ ID NO:41)
 P   S   I   R   I   T

CCAAGTATTCAAATTACA          (SEQ ID NO:72)
 P   S   I   Q   I   T

CCAAGTATTCAAATCACA          (SEQ ID NO:86)
 P   S   I   Q   I   T

CCAAGTATCCAATTTACA          (SEQ ID NO:42)
 P   S   I   Q   F   T

AGCCCTCGGATCGAGATCACT       (SEQ ID NO:43)
 S   P   R   I   E   I   T

AGTCCTCGCATCGAGATAACC       (SEQ ID NO:87)
 S   P   R   I   E   I   T

TGTCCCAGCATCCGCATCACC       (SEQ ID NO:44)
 C   P   S   I   R   I   T

TGCCCAAGTATTCAAATTACA       (SEQ ID NO:45)
 C   P   S   I   Q   I   T

TGCCCAAGTATTCAAATCACA       (SEQ ID NO:88)
 C   P   S   I   Q   I   T

TGCCCAAGTATCCAATTTACA       (SEQ ID NO:46)
 C   P   S   I   Q   F   T
```

Fig. 2 (continued)

```
AGCCCTCGGATCGAGATCACTCCA        (SEQ ID NO:47)
 S   P   R   I   E   I   T   P

AGCCCTCGGATCGAGATCACTCCG        (SEQ ID NO:89)
 S   P   R   I   E   I   T   P

AGTCCTCGCATCGAGATAACCTCG        (SEQ ID NO:48)
 S   P   R   I   E   I   T   S

TGTCCCAGCATCCGCATCACCTCC        (SEQ ID NO:49)
 C   P   S   I   R   I   T   S

TGCCCAAGTATTCAAATTACATCT        (SEQ ID NO:50)
 C   P   S   I   Q   I   T   S

TGCCCAAGTATTCAAATCACATCC        (SEQ ID NO:90)
 C   P   S   I   Q   I   T   S

TGCCCAAGTATCCAATTTACATCT        (SEQ ID NO:51)
 C   P   S   I   Q   F   T   S

AGCCCTCGGATCGAGATCACTCCATCC     (SEQ ID NO:52)
 S   P   R   I   E   I   T   P   S

AGCCCTCGGATCGAGATCACTCCGTCC     (SEQ ID NO:91)
 S   P   R   I   E   I   T   P   S

AGTCCTCGCATCGAGATAACCTCGTGC     (SEQ ID NO:53)
 S   P   R   I   E   I   T   S   C

TGTCCCAGCATCCGCATCACCTCCATC     (SEQ ID NO:54)
 C   P   S   I   R   I   T   S   I

TGCCCAAGTATTCAAATTACATCTATC     (SEQ ID NO:55)
 C   P   S   I   Q   I   T   S   I

TGCCCAAGTATTCAAATCACATCCATT     (SEQ ID NO:92)
 C   P   S   I   Q   I   T   S   I

TGCCCAAGTATCCAATTTACATCTATC     (SEQ ID NO:56)
 C   P   S   I   Q   F   T   S   I
```

Fig. 2 (continued)

```
TCGGGCCCGAGCCCTCGGATCGAGATCACTCCATCCCAC        (SEQ ID NO:57)
 S   G   P   S   P   R   I   E   I   T   P   S   H

TCGGGCCTGAGCCCTCGGATCGAGATCACTCCGTCCCAC        (SEQ ID NO:58)
 S   G   L   S   P   R   I   E   I   T   P   S   H

GCCCTGGAGAGTCCTCGCATCGAGATAACCTCGTGCTTG        (SEQ ID NO:59)
 A   L   E   S   P   R   I   E   I   T   S   C   L

GTTCTCGAGTGTCCCAGCATCCGCATCACCTCCATCTCT        (SEQ ID NO:60)
 V   L   E   C   P   S   I   R   I   T   S   I   S

CCCTTTGAGTGCCCAAGTATTCAAATTACATCTATCTCT        (SEQ ID NO:61)
 P   F   E   C   P   S   I   Q   I   T   S   I   S

CCCTTTGAGTGCCCAAGTATTCAAATCACATCCATTTCT        (SEQ ID NO:62)
 P   F   E   C   P   S   I   Q   I   T   S   I   S

CCCTTTGAGTGCCCAAGTATCCAATTTACATCTATCTCT        (SEQ ID NO:63)
 P   F   E   C   P   S   I   Q   F   T   S   I   S

AAGCCAGCAGGGGCTTCGGGCCCGAGCCCTCGGATCGAGATCACTCCATCCCACGAACTG
 K   P   A   G   A   S   G   P   S   P   R   I   E   I   T   P   S   H   E   L

ATGCAGGCAGGGGGG       (SEQ ID NO:64)
 M   Q   A   G   G

AAGCCAGCAGGGGCCTCGGGCCTGAGCCCTCGGATCGAGATCACTCCGTCCCACGAACTG
 K   P   A   G   A   S   G   L   S   P   R   I   E   I   T   P   S   H   E   L

ATCCAGGCAGTGGGG       (SEQ ID NO:65)
 I   Q   A   V   G

CCTGATGGGGCCCCTGCCCTGGAGAGTCCTCGCATCGAGATAACCTCGTGCTTGGGCCTG
 P   D   G   A   P   A   L   E   S   P   R   I   E   I   T   S   C   L   G   L

TACCACAACAATAAC       (SEQ ID NO:66)
 Y   H   N   N   N
```

Fig. 2 (continued)

```
GCTGGGGGTGGCCGTGTTCTCGAGTGTCCCAGCATCCGCATCACCTCCATCTCTCCCACG
 A  G  G  G  R  V  L  E  C  P  S  I  R  I  T  S  I  S  P  T

CCGGAGCCGCCAGCA      (SEQ ID NO:67)
 P  E  P  P  A

TTAGGTGGTCCCAAACCCTTTGAGTGCCCAAGTATTCAAATTACATCTATCTCTCCTAAC
 L  G  G  P  K  P  F  E  C  P  S  I  Q  I  T  S  I  S  P  N

TGTCATCAAGAATTA      (SEQ ID NO:68)
 C  H  Q  E  L

TTAGGTGGTCCTAAACCCTTTGAGTGCCCAAGTATTCAAATCACATCCATTTCTCCTAAC
 L  G  G  P  K  P  F  E  C  P  S  I  Q  I  T  S  I  S  P  N

TGTCATCAAGGAACA      (SEQ ID NO:69)
 C  H  Q  G  T

TTAGGTGGTCCCAAACCCTTTGAGTGCCCAAGTATCCAATTTACATCTATCTCTCCTAAC
 L  G  G  P  K  P  F  E  C  P  S  I  Q  F  T  S  I  S  P  N

TGTCAACAAGAATTA      (SEQ ID NO:70)
 C  Q  Q  E  L
```

US 7,816,490 B2

SPECIFIC INHIBITORS OF NFAT ACTIVATION BY CALCINEURIN AND THEIR USE IN TREATING IMMUNE-RELATED DISEASES

RELATED APPLICATIONS

This application is a divisional of U.S. application Ser. No. 11/474,218, filed Jun. 23, 2006, now abandoned which is a continuation of U.S. application Ser. No. 10/066,151, filed Jan. 31, 2002, now U.S. Pat. No. 7,084,241, which is a continuation of application Ser. No. 09/248,620, filed Feb. 11, 1999, now abandoned, which claims the benefit of U.S. Provisional Application No. 60/074,467, filed Feb. 12, 1998, each of which are incorporated herein by reference in their entirety.

The U.S. Government has a paid-up license in this invention and the right in limited circumstances to require the patent owner to license others on reasonable terms as provided for by the terms of Grant No. AI 40127 awarded by the National Institutes of Health.

FIELD OF THE INVENTION

This invention relates generally to NFAT peptide fragments, NFAT polynucleotides, NFAT gene therapy vectors, treatments for immune system related diseases, and methods for identifying immunosuppressive agents.

BACKGROUND OF THE INVENTION

Hyperactivity or inappropriate activity of the immune system is a serious and widespread medical problem. It contributes to acute and chronic immune diseases, e.g., allergic and atopic diseases, e.g., asthma, allergic rhinitis, allergic conjunctivitis and atopic dermatitis, and to autoimmune diseases, e.g., rheumatoid arthritis, insulin-dependent diabetes, inflammatory bowel disease, autoimmune thyroiditis, hemolytic anemia and multiple sclerosis. Hyperactivity or inappropriate activity of the immune system is also involved in transplant graft rejections and graft-versus-host disease.

A certain family of transcription factors, the NFAT proteins, are expressed in immune cells and play a key role in eliciting immune responses. The NFAT proteins are activated by calcineurin, and the activated NFAT proteins, in turn, induce transcription of cytokine genes which are required for an immune response. The immunosuppressive drugs cyclosporin A and FK506 are potent inhibitors of cytokine gene transcription in activated immune cells, and have been reported to act by inhibiting calcineurin such that calcineurin is not able to activate NFAT. These drugs, however, can display nephrotoxic and neurotoxic effects after long term usage. Since calcineurin is ubiquitously expressed in many tissues, the drugs' inhibition of calcineurin activity toward substrates other than NFAT may contribute to the observed toxicity.

There is a need for immunosuppressive agents which selectively inhibit the calcineurin-NFAT interactions and which do not inhibit the enzymatic activity of calcineurin for its other substrates.

SUMMARY OF THE INVENTION

It is an object of the invention to provide an immunosuppressive agent with reduced toxic effects.

It is another object of the invention to provide an immunosuppressive agent that inhibits interaction between calcineurin and NFAT.

It is yet another object of the invention to provide an immunosuppressive agent that selectively inhibits interaction between calcineurin and NFAT, and which does not inhibit enzymatic activity of calcineurin for its other substrates.

It is yet another object of the invention to provide a gene therapy vector encoding an immunosuppressive agent that selectively inhibits interaction between calcineurin and NFAT.

It is yet another object of the invention to provide a method for inhibiting an immune response using an immunosuppressive agent that selectively inhibits interaction between calcineurin and NFAT.

It is yet another object of the invention to provide methods for high-throughput screening of candidate agents to identify agents that inhibit one or more aspects of calcineurin-mediated NFAT activation.

According to the invention, an isolated fragment of the conserved regulatory domain of NFAT protein, e.g., NFAT1, NFAT2, NFAT3 or NFAT4, capable of inhibiting protein-protein interaction between calcineurin and NFAT, or a biologically active analog thereof, is provided. Preferably, the peptide fragment or biologically active analog thereof does not inhibit or does not substantially inhibit the activity of calcineurin toward non-NFAT calcineurin substrates.

In certain embodiments, the peptide fragment comprises the amino acid sequence $IX_2X_3T$ (SEQ ID NO:104), wherein $X_2$ is E, R or Q, and $X_3$ is I or F. Preferred amino acid sequences are, e.g., IEIT (SEQ ID NO:105), IRIT (SEQ ID NO:106), IQIT (SEQ ID NO:107), and IQFT (SEQ ID NO:108).

In certain embodiments, the peptide fragment comprises the amino acid sequence $X_1IX_2X_3T$ (SEQ ID NO:73), wherein $X_1$ is R or S, $X_2$ is E, R or Q, and $X_3$ is I or F. Preferred amino acid sequences are, e.g., $X_1IX_2IT$ (SEQ ID NO:74), RIXIT (SEQ ID NO:75), $X_1IEIT$ (SEQ ID NO:76), RIEIT (SEQ ID NO:1), SIRIT (SEQ ID NO:2), SIQIT (SEQ ID NO:3), and SIQFT (SEQ ID NO:4).

In certain embodiments, the peptide fragment comprises the amino acid sequence $PX_1IX_2X_3T$ (SEQ ID NO:77), wherein $X_1$ is R or S, $X_2$ is E, R or Q, and $X_3$ is I or F. Preferred amino acid sequences are, e.g., PRIEIT (SEQ ID NO:5), PSIRIT (SEQ ID NO:6), PSIQIT (SEQ ID NO:71) and PSIQFT (SEQ ID NO:7).

In certain embodiments, the peptide fragment comprises the amino acid sequence $X_5PX_1IX_2X_3T$ (SEQ ID NO:78), wherein $X_1$ is R or S, $X_2$ is E, R or Q, $X_3$ is I or F and $X_5$ is S or C. Preferred amino acid sequences are, e.g., SPRIEIT (SEQ ID NO:8), CPSIRIT (SEQ ID NO:9), CPSIQIT (SEQ ID NO:10) and CPSIQFT (SEQ ID NO:11).

In certain embodiments, the peptide fragment comprises the amino acid sequence $X_5PX_1IX_2X_3TX_6$ (SEQ ID NO:79), wherein $X_1$ is R or S, $X_2$ is E, R or Q, $X_3$ is I or F, $X_5$ is S or C, and $X_6$ is P or S. Preferred amino acid sequences are, e.g., SPRIEITP (SEQ ID NO:12), SPRIEITS (SEQ ID NO:13), CPSIRITS (SEQ ID NO:14), CPSIQITS (SEQ ID NO:15) and CPSIQFTS (SEQ ID NO:16).

In certain embodiments, the peptide fragment comprises the amino acid sequence $X_5PX_1IX_2X_3TX_6X_7$ (SEQ ID NO:80), wherein $X_1$ is R or S, $X_2$ is E, R or Q, $X_3$ is I or F, $X_5$ is S or C, $X_6$ is P or S, and $X_7$ is S, C or I. Preferred amino acid sequences are SPRIEITPS (SEQ ID NO:17), SPRIEITSC (SEQ ID NO:18), CPSIRITSI SEQ ID NO:19), CPSIQITSI (SEQ ID NO:20), and CPSIQFTSI (SEQ ID NO:21).

In certain embodiments, the peptide fragment comprises the amino acid sequence $X_{11}X_{10}X_9X_5PX_1IX_2X_3TX_6X_7X_8$ (SEQ ID NO:81), wherein $X_1$ is R or S, $X_2$ is E, R or Q, $X_3$ is I or F, $X_5$ is S or C, $X_6$ is P or S, $X_7$ is S, C or I, $X_8$ is H, L or S, $X_9$ is P, L or E, $X_{10}$, is G, L or F, and $X_{10}$ is S, A, V or P. Preferred amino acid sequences are, e.g., SGPSPRIEITPSH (SEQ ID NO:22), SGLSPRIEITPSH (SEQ ID NO:23), ALESPRIEITSCL (SEQ ID NO:24), VLECPSIRITSIS (SEQ ID NO:25), PFECPSIQITSIS (SEQ ID NO:26), PFECPSIQITSIS (SEQ ID NO:27) and PFECPSIQFTSIS (SEQ ID NO:28). Other preferred amino acid sequences are, e.g., KPAGASGPSPRIEITPSHELMQAGG (SEQ ID NO:29), KPAGASGLSPRIEITPSHELIQAVG (SEQ ID NO:30), PDGAPALESPRIEITSCLGLYHNNN (SEQ ID NO:31), AGGGRVLECPSIRITSISPTPEPPA (SEQ ID NO:32), LGGPKPFECPSIQITSISPNCHQEL (SEQ ID NO:33), LGGPKPFECPSIQITSISPNCHQGT (SEQ ID NO:34) and LGGPKPFECPSIQFTSISPNCQQEL (SEQ ID NO:35).

Another aspect of the invention is an isolated polynucleotide encoding the peptide comprising the amino acid sequence as set forth in SEQ ID NO:105, SEQ ID NO:106, SEQ ID NO:107, SEQ ID NO:108, or biologically active analogs thereof. Preferred polynucleotide sequences are, e.g., the sequences as set forth in SEQ ID NO:109, SEQ ID NO:110, SEQ ID NO:111, SEQ ID NO:112, SEQ ID NO:113 and SEQ ID NO:114.

Another aspect of the invention is an isolated polynucleotide encoding the peptide comprising the amino acid sequence as set forth in SEQ ID NO:1, SEQ ID NO:2, SEQ ID NO:3, SEQ ID NO:4, or biologically active analogs thereof. Preferred polynucleotide sequences are, e.g., the sequences as set forth in SEQ ID NO:36, SEQ ID NO:37, SEQ ID NO:38, SEQ ID NO:39, SEQ ID NO:83 and SEQ ID NO:84.

Another aspect of the invention is an isolated polynucleotide encoding the peptide comprising the amino acid sequence as set forth in SEQ ID NO:5, SEQ ID NO:6, SEQ ID NO:71, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or biologically active analogs thereof. Preferred polynucleotide sequences are, e.g., the sequences as set forth in SEQ ID NO:40, SEQ ID NO:41, SEQ ID NO:72, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:85, SEQ ID NO:86, SEQ ID NO:87, SEQ ID NO:88, SEQ ID NO:89, SEQ ID NO:90, SEQ ID NO:91 and SEQ ID NO:92.

Another aspect of the invention is an isolated polynucleotide encoding the peptide comprising the amino acid sequence as set forth in SEQ ID NO:22, SEQ ID NO:23, SEQ ID NO:24, SEQ ID NO:25, SEQ ID NO:26, SEQ ID NO:27, SEQ ID NO:28, or biologically active analogs thereof. Preferred polynucleotide sequences are, e.g., the sequences as set forth in SEQ ID NO:57, SEQ ID NO:58, SEQ ID NO:59, SEQ ID NO:60, SEQ ID NO:61, SEQ ID NO:62 and SEQ ID NO:63.

Another aspect of the invention is an isolated polynucleotide encoding the peptide comprising the amino acid sequence as set forth in SEQ ID NO:29, SEQ ID NO:30, SEQ ID NO:31, SEQ ID NO:32, SEQ ID NO:33, SEQ ID NO:34, SEQ ID NO:35, or biologically active analogs thereof. Preferred polynucleotide sequences are, e.g., sequences as set forth in SEQ ID NO:64, SEQ ID NO:65, SEQ ID NO:66, SEQ ID NO:67, SEQ ID NO:68, SEQ ID NO:69 and SEQ ID NO:70.

Another aspect of the invention is a gene therapy vector comprising a nucleotide sequence encoding a peptide fragment of the conserved regulatory domain of NFAT protein capable of inhibiting protein-protein interaction between calcineurin and NFAT, or a biologically active analog of the peptide fragment.

In preferred embodiments, the gene therapy vector comprises a nucleotide sequence encoding the peptide comprising the amino acid sequence as set forth in SEQ ID NO:105, SEQ ID NO:106, SEQ ID NO:107, SEQ ID NO:108, or biologically active analogs thereof. In certain embodiments, the gene therapy vector comprises the nucleotide sequences as set forth in SEQ ID NO:109, SEQ ID NO:110, SEQ ID NO:111, SEQ ID NO:112, SEQ ID NO:113 or SEQ ID NO:114.

In preferred embodiments, the gene therapy vector comprises a nucleotide sequence encoding the peptide comprising the amino acid sequence as set forth in SEQ ID NO:1, SEQ ID NO:2, SEQ ID NO:3, SEQ ID NO:4, or biologically active analogs thereof. In certain embodiments, the gene therapy vector comprises the nucleotide sequences as set forth in SEQ ID NO:36, SEQ ID NO:37, SEQ ID NO:38, SEQ ID NO:39, SEQ ID NO:83 or SEQ ID NO:84.

In preferred embodiments, the gene therapy vector comprises a nucleotide sequence encoding the peptide comprising the amino acid sequence as set forth in SEQ ID NO:5, SEQ ID NO:6, SEQ ID NO:71, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or biologically active analogs thereof. In certain embodiments, the gene therapy vector comprises the nucleotide sequence as set forth in SEQ ID NO:40, SEQ ID NO:41, SEQ ID NO:72, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:85, SEQ ID NO:86, SEQ ID NO:87, SEQ ID NO:88, SEQ ID NO:89, SEQ ID NO:90, SEQ ID NO:91 and SEQ ID NO:92.

In preferred embodiments, the gene therapy vector comprises a nucleotide sequence encoding the peptide comprising the amino acid sequence as set forth in SEQ ID NO:22, SEQ ID NO:23, SEQ ID NO:24, SEQ ID NO:25, SEQ ID NO:26, SEQ ID NO:27, SEQ ID NO:28, or biologically active analogs thereof. In certain embodiments, the gene therapy vector comprises the nucleotide sequence as set forth in SEQ ID NO:57, SEQ ID NO:58, SEQ ID NO:59, SEQ ID NO:60, SEQ ID NO:61, SEQ ID NO:62 or SEQ ID NO:63.

In preferred embodiments, the gene therapy vector comprises a nucleotide sequence encoding the peptide comprising the amino acid sequence as set forth in SEQ ID NO:29, SEQ ID NO:30, SEQ ID NO:31, SEQ ID NO:32, SEQ ID NO:33, SEQ ID NO:34 and SEQ ID NO:35, or biologically active analogs thereof. In certain embodiments, the gene therapy vector comprises the nucleotide sequence as set forth in SEQ ID NO:64, SEQ ID NO:65, SEQ ID NO:66, SEQ ID NO:67, SEQ ID NO:68, SEQ ID NO:69 or SEQ ID NO:70.

Another aspect of the invention is a cell having a gene therapy vector described herein.

Another aspect of the invention is a method for producing a peptide capable of inhibiting protein-protein interaction between calcineurin and NFAT, comprising culturing a cell having a gene therapy vector described herein under conditions that permit expression of the peptide.

Another aspect of the invention is a method for treating an immune-related disease or condition, e.g., acute immune diseases, chronic immune diseases or autoimmune diseases, in an animal. It is also meant to include treatment of tissue or organ transplant graft rejections or graft-versus-host disease. A gene therapy vector described herein is administered to the animal.

Another aspect of the invention is a method for providing an animal having an immune-related disease or condition with a therapeutically effective level of a peptide capable of inhibiting protein-protein interaction between calcineurin and NFAT. A gene therapy vector described herein is administered to the animal.

Another aspect of the invention is a method for inhibiting an immune response in an animal. An animal in need of inhibition of an immune response is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered to the animal so as to inhibit the immune response in the animal.

In certain embodiments, the therapeutically effective amount of the peptide fragment is provided by providing to the animal a recombinant nucleic acid having a nucleotide sequence encoding the peptide fragment or a biologically active analog thereof, and which is capable of expressing the peptide fragment or biologically active analog thereof in vivo. The peptide fragment is administered to the animal by administering the recombinant nucleic acid. The nucleic acid can be, e.g., any of the polynucleotides described herein.

In certain embodiments, the therapeutically effective amount of the peptide fragment is provided by providing to the animal a composition comprising animal cells wherein a recombinant nucleic acid having a nucleotide sequence encoding the peptide fragment has been introduced ex vivo into the animal cells so as to express the peptide fragment in the animal cells. The peptide fragment is administered to the animal by administering the animal cells having the recombinant nucleic acid. Preferably, the recombinant nucleic acid is a gene therapy vector, e.g., as described herein. Preferably, the animal cells are derived from the animal to be treated or allogeneic cells.

Another aspect of the invention is a method for treating a disease involving hyperactivity or inappropriate activity of the immune system, a transplant graft rejection or graft-versus-host disease, in an animal. An animal in need of treatment for a disease involving hyperactivity or inappropriate activity of the immune system, a transplant graft rejection or graft-versus-host disease, is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered to the animal in a therapeutically effective amount such that treatment of the disease involving hyperactivity or inappropriate activity of the immune system, transplant graft rejection or graft-versus-host disease, occurs.

Another aspect of the invention is a method for treating an animal at risk for a disease involving hyperactivity or inappropriate activity of the immune system, a transplant graft rejection or graft-versus-host disease. An animal at risk for a disease involving hyperactivity or inappropriate activity of the immune system, a transplant graft rejection or graft-versus-host disease, is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered in a therapeutically effective amount such that treatment occurs.

Another aspect of the invention is a method for gene therapy. An animal cell is genetically modified such that it is able to express a peptide fragment or biologically active analog thereof of the conserved regulatory domain of NFAT protein, the peptide fragment being capable of inhibiting calcineurin-mediated NFAT activation, so as to effect gene therapy. In certain embodiments, the animal cells are genetically modified by introducing into the cells a recombinant nucleic acid having a nucleotide sequence encoding the peptide fragment and which is capable of expressing the peptide fragment in vivo. Preferably, the recombinant nucleic acid is a gene therapy vector, e.g., as described herein.

Another aspect of the invention is a pharmaceutical composition for treating an immune-related disease or condition in an animal comprising a therapeutically effective amount of a peptide fragment of the conserved regulatory domain of NFAT protein capable of inhibiting protein-protein interaction between calcineurin and NFAT, or a biologically active analog thereof, and a pharmaceutically acceptable carrier. The peptide fragment can be, e.g., any of the peptide fragments described herein.

Another aspect of the invention is a pharmaceutical composition for treating an immune-related disease or condition in an animal, comprising a therapeutically effective amount of a recombinant nucleic acid having a nucleotide sequence encoding a peptide fragment of the conserved regulatory domain of NFAT protein capable of inhibiting protein-protein interaction between calcineurin and NFAT, or a biologically active analog thereof, and a pharmaceutically acceptable carrier. The nucleic acid can be, e.g., any of the polynucleotides described herein.

Another aspect of the invention is a pharmaceutical composition for treating an immune-related disease or condition in an animal, comprising a therapeutically effective amount of animal cells wherein a recombinant nucleic acid having a nucleotide sequence encoding a peptide fragment of the conserved regulatory domain of NFAT protein capable of inhibiting protein interaction between calcineurin and NFAT, or a biologically active analog thereof, has been introduced into the animal cells so as to express the peptide fragment; and a pharmaceutically acceptable carrier. Preferably, the animal cells are cells derived from the animal to be treated or allogeneic cells.

Another aspect of the invention is a method for inhibiting protein-protein interaction between calcineurin and NFAT in vivo. A cell having calcineurin and NFAT is provided. A peptide fragment or a biologically active analog thereof of the conserved regulatory domain of NFAT protein capable of inhibiting protein-protein interaction between calcineurin and NFAT is provided. The calcineurin and peptide fragment or biologically active analog thereof are contacted in vivo such that protein-protein interaction between the calcineurin and the NFAT is inhibited.

Another aspect of the invention is a method for inhibiting protein-protein interaction between calcineurin and NFAT in vitro. Calcineurin and NFAT are provided. A peptide fragment or a biologically active analog thereof of the conserved regulatory domain of NFAT protein capable of inhibiting protein-protein interaction between calcineurin and NFAT is provided. The calcineurin and peptide fragment or biologically active analog thereof are contacted in vitro such that protein-protein interaction between the calcineurin and the NFAT is inhibited.

Another aspect of the invention is a method for evaluating an agent for use in modulating an immune response. A cell is provided. An agent, e.g., a peptide fragment of the conserved regulatory domain of NFAT protein or biologically active analogs thereof, is provided. The effect of the agent on an aspect of calcineurin-mediated NFAT activation is evaluated, e.g., protein-protein interaction between calcineurin and NFAT, dephosphorylation of NFAT by calcineurin, recruitment of NFAT to the nucleus in a cell, conformational change in NFAT, or activation of NFAT-dependent gene transcription. A change in the aspect of calcineurin-mediated NFAT activation is indicative of the usefulness of the agent in modulating an immune response.

Another aspect of the invention is a method for high throughput screening of candidate agents to identify an agent that inhibits protein-protein interaction between calcineurin and NFAT. A first compound is provided. The first compound is calcineurin or a biologically active derivative thereof, or the first compound is NFAT or a biologically active derivative thereof. A second compound is provided which is different from the first compound and which is labeled. The second compound is calcineurin or a biologically active derivative thereof, or the second compound is NFAT or a biologically active derivative thereof. A candidate agent is provided. The first compound, second compound and candidate agent are contacted with each other. The amount of label bound to the first compound is determined. A reduction in protein-protein interaction between the first compound and the second compound as assessed by label bound is indicative of the usefulness of the agent in inhibiting protein-protein interaction between calcineurin and NFAT. In certain embodiments, the method includes a washing step after the contacting step, so as to separate bound and unbound label.

Another aspect of the invention is a method for high-throughput screening of candidate agents to identify an agent that inhibits dephosphorylation of NFAT by calcineurin. Phosphorylated NFAT is provided. Calcineurin or a biologically active derivative thereof having enzymatic activity is provided. A candidate agent is provided. The phosphorylated NFAT, the calcineurin or biologically active derivative thereof, and the candidate agent are contacted with each other in reaction media, e.g., buffer, under conditions that allow enzymatic activity of calcineurin. In certain embodiment, the NFAT is separated from the reaction media. It is determined whether phosphate remains associated with the NFAT. If phosphate remains associated with NFAT, it is indicative of the usefulness of the agent in inhibiting dephosphorylation of NFAT by calcineurin.

Another aspect of the invention is a method for high-throughput screening of candidate agents to identify an agent that inhibits conformational change in NFAT from dephosphorylation by calcineurin. Phosphorylated NFAT is provided. Calcineurin or a biologically active derivative thereof having enzymatic activity is provided. A candidate agent is provided. An oligonucleotide having an NFAT site is provided. The phosphorylated NFAT, calcineurin or biologically active derivative thereof, and the candidate agent are contacted with each other in reaction media under conditions that allow enzymatic activity of calcineurin. Specific binding of NFAT to the oligonucletide having the NFAT site is determined. A reduction of binding is indicative of the usefulness of the agent in inhibiting conformational change in NFAT from dephosphorylation by calcineurin.

Another aspect of the invention is a method for high-throughput screening of candidate agents to identify an agent that inhibits calcineurin-dependent import of NFAT into the nucleus of a cell. Cells expressing NFAT are provided. A stimulant that activates NFAT through the calcium/calcineurin pathway is provided. A candidate agent is provided. The cells, stimulant and candidate agent are contacted with each other. The presence or absence of nuclear NFAT in the cells is determined. A reduction in nuclear NFAT is indicative of the agent inhibiting calcineurin-dependent import of NFAT into the nucleus of a cell.

Another aspect of the invention is a method for assessing the state of NFAT activation of immune system cells from an animal. Immune system cells isolated from an animal are provided. The presence or absence of nuclear NFAT in the cells is determined. The presence of nuclear NFAT in the cells is indicative of activation of NFAT in the cells.

Another aspect of the invention is a method for assessing the ability of immune system cells isolated from an animal to respond to an NFAT activating signal. Immune system cells from an animal are provided, the cells being unactivated for NFAT. A stimulant that activates NFAT is provided. The cells are contacted with the stimulant. The presence or absence of nuclear NFAT in the cells is determined. A reduction in nuclear NFAT is indicative of impairment of the ability of the cells to respond to an NFAT activating signal.

Another aspect of the invention is a method for identifying a stimulant that can activate NFAT in immune system cells isolated from an animal. Immune system cells isolated from an animal are provided. A candidate stimulant, e.g., allergen, is provided. The cells are contacted with the candidate stimulant. The presence or absence of nuclear NFAT in the cells is determined. The presence of nuclear NFAT is indicative of the stimulant activating NFAT in the cells.

Another aspect of the invention is a method for identifying an allergen. An animal cell line expressing NFAT is provided. IgE from an animal, e.g., a human, is provided. A candidate allergen is provided. The cell line is contacted with the IgE. The cell line is contacted with the candidate allergen. The presence or absence of nuclear NFAT in cells of the cell line is determined. The presence of nuclear NFAT is indicative of the candidate allergen being an allergen.

The above and other features, objects and advantages of the present invention will be better understood by a reading of the following specification in conjunction with the drawings.

BRIEF DESCRIPTION OF THE DRAWINGS

FIG. 1 depicts amino acid sequences of certain immunosuppressive agents of this invention, including 5-mers, 6-mers, 7-mers, 8-mers, 9-mers, 13-mers and 25-mers.

FIG. 2 depicts cDNA sequences from murine NFAT1, human NFAT1, human NFAT2, human NFAT3, human NFAT4 and murine NFAT4, encoding certain immunosuppressive agents of this invention, and the corresponding amino acid sequences.

DETAILED DESCRIPTION

This invention provides an isolated fragment of the conserved regulatory domain of NFAT protein capable of inhibiting protein-protein interaction between calcineurin and NFAT, or a biologically active analog thereof.

By NFAT protein (nuclear factor of activated T cells) is meant a member of a family of transcription factors comprising the members NFAT1, NFAT2, NFAT3 and NFAT4, with several isoforms. Any other NFAT protein whose activation is calcineurin dependent is also meant to be included. NFAT proteins can be, e.g., mammalian proteins, e.g., human or murine. NFAT1, NFAT2 and NFAT4 are expressed in immune cells, e.g., T lymphocytes, and play a role in eliciting immune responses. NFAT proteins are involved in the transcriptional regulation of cytokine genes, e.g., IL-2, IL-3, IL-4, TNF-α and IFN-γ, during the immune response.

cDNA sequences for NFAT have been previously reported. See McCaffrey et al., Science 262:750-754 (1993) and Luo et al., Mol. Cell Biol. 16:3955-3966 (1996) for murine NFAT1. See Luo et al., Mol. Cell Biol. 16:3955-3966 (1996) for human NFAT1. See Northrop et al., Nature 369:497-502 (1994) for human NFAT2, and Park et al., J. Biol. Chem. 271:20914-20921 (1996) for human NFAT2b. The published sequences for human NFAT2 represent two isoforms differing by alternative splicing at the N and C termini, but having the same regulatory domain and DNA-binding domain. See Hoey et al., Immunity 2:461-472 (1995) for human NFAT3. See Masuda et al., Mol. Cell Biol. 15:2697-2706 (1995) and Hoey et al., Immunity 2:461-472 (1995) for human NFAT4. See Ho et al., J. Biol. Chem. 270:19898-19907 (1995) and Liu et al., Mol. Cell Biol. 8:157-170 (1997) for murine NFAT4. The two published sequences for murine NFAT4 are not identical.

NFAT proteins have been shown to be direct substrates of calcineurin. Calcineurin is a calmodulin-dependent, cyclosporin A/FK506-sensitive, phosphatase. Calcineurin is activated through its interaction with $Ca^{+2}$ activated calmodulin when intracellular calcium levels are elevated as a result of receptor crosslinking and phospholipase C activation. The activated calcineurin in turn activates NFAT from an inactive cytoplasmic pool. NFAT activation involves protein-protein interaction between calcineurin and NFAT, dephosphorylation of NFAT by calcineurin, conformational change in NFAT resulting from the interaction between calcineurin and NFAT or the dephosphorylation of NFAT and translocation of NFAT to the nucleus. NFAT activation results in induction of NFAT-dependent gene expression of, e.g., cytokine genes.

The conserved regulatory domain of NFAT is an N-terminal region of NFAT which is about 300 amino acids in length. The conserved regulatory domain of murine NFAT1 is a region extending from amino acid residue 100 through amino acid residue 397, of human NFAT1 is a region extending from amino acid residue 100 through 395, of human NFAT2 is a region extending from amino acid residue 106 through 413, of human NFAT2b is a region extending from amino acid residue 93 through 400, of human NFAT3 is a region extending from amino acid residue 102 through 404, and of human NFAT4 is a region extending from amino acid residue 97 through 418. The conserved regulatory domain is moderately conserved among the members of the NFAT family, NFAT1, NFAT2, NFAT3 and NFAT4. The conserved regulatory region binds directly to calcineurin. The conserved regulatory region is located immediately N-terminal to the DNA-binding domain (amino acid residues 398 through 680 in murine NFAT1, amino acid residues 396 through 678 in human NFAT1, amino acid residues 414 through 696 in human NFAT2, amino acid residues 401 through 683 in human NFAT2b, amino acid residues 405 through 686 in human NFAT3, and amino acid residues 419 through 700 in human NFAT4).

In certain embodiments of the invention, the peptide fragment or biologically active analog thereof is further capable of inhibiting dephosphorylation of NFAT by calcineurin. In certain embodiments, the peptide fragment or biologically active analog thereof is further capable of inhibiting recruitment of NFAT to the nucleus in a cell. In certain embodiments, the peptide fragment or biologically active analog thereof is further capable of inhibiting conformational change in NFAT that results from the protein-protein interaction between NFAT and calcineurin or from the dephosphorylation of NFAT by calcineurin. In certain embodiments, the peptide fragment or biologically active analog thereof is further capable of inhibiting NFAT-dependent gene transcription.

Preferably, the peptide fragment or biologically active analog thereof does not inhibit or does not substantially inhibit the activity of calcineurin toward non-NFAT calcineurin substrates. Calcineurin normally is capable of interacting with many different substrates, e.g., NFAT and the microtubule-associated protein tau (Fleming and Johnson, Biochem J 309: 41-47 (1995); Yamamoto et al, J Biochem 118:1224-1231 (1995)), the regulatory subunit RII of cAMP-dependent protein kinase (Blumenthal and Krebs, Biophys J 41:409a (1983)), inhibitor-1 (Hemmings et al, Nature 310:503-505 (1984); Mulkey et al, Nature 369:486-488 (1994)), dopamine- and cAMP-regulated phosphoprotein DARPP-32 (Hemmings et al, Nature 310:503-505 (1984)), a dihydropyridine-sensitive voltage-dependent $Ca^{2+}$ channel (Hosey et al, Proc Natl Acad Sci USA 83:3733-3737 (1986)), nitric oxide synthase (Dawson et al, Proc Natl Acad Sci USA 90:9808-9812 (1993)), dynamin (Liu et al, Science 265:970-973 (1994); Nichols et al, J Biol Chem 269:23817-23823 (1994)), the inositol 1,4,5-trisphosphate receptor-FKBP12 complex (Cameron et al, Cell 83:463-472 (1995)), and the ryanodine receptor-FKBP12 complex (Cameron et al, Cell 83:463-472 (1995)). A key advantage of this invention is that it includes peptide fragments and analogs thereof which are specific for the interaction between calcineurin and NFAT. Such specific inhibitors can be used for therapeutic purposes with reduced toxic effects, as compared to general immuno suppressants.

By fragment of the conserved regulatory domain of NFAT protein is meant some portion of the naturally occurring conserved regulatory domain of NFAT protein. Preferably, the fragment is less than about 150 amino acid residues, more preferably is less than about 100 amino acid residues, more preferably yet is less than about 50 amino acid residues, more preferably yet is less than about 30 amino acid residues, more preferably yet is less than about 20 amino acid residues, more preferably yet is less than about 10 amino acid residues, and most preferably is less than about 6 amino acid residues in length. Preferably, the fragment is greater than about 3 amino acid residues in length. Fragments include, e.g., truncated secreted forms, cleaved fragments, proteolytic fragments, splicing fragments, other fragments, and chimeric constructs between at least a portion of the relevant gene and another molecule. Fragments of the conserved regulatory domain of NFAT protein can be generated by methods known to those skilled in the art. In preferred embodiments, the fragment is biologically active. The ability of a candidate fragment to exhibit a biological activity of the conserved regulatory domain of NFAT can be assessed by, e.g., its ability to form a protein-protein interaction with calcineurin, or its ability to inhibit the binding of NFAT to calcineurin, by methods as described herein. Also included are fragments containing residues that are not required for biological activity of the fragment or that result from alternative mRNA splicing or alternative protein processing events.

Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated, e.g., by random shearing, restriction digestion, chemical synthesis of oligonucleotides, amplification of DNA using the polymerase chain reaction, or a combination of the above-discussed methods.

Fragments can also be chemically synthesized using techniques known in the art, e.g., conventional Merrifield solid phase f-Moc or t-Boc chemistry. For example, peptides of the present invention can be arbitrarily divided into fragments of desired length with no overlap of the fragments, or divided into overlapping fragments of a desired length.

An NFAT protein used for generating analogs or fragments can be obtained, e.g., from purification or secretion of a naturally occurring NFAT protein, from recombinant NFAT protein, or from synthesized NFAT protein.

In certain embodiments, the peptide fragment comprises the amino acid sequence $IX_2X_3T$ (SEQ ID NO:104), wherein $X_2$ is E, R or Q, and $X_3$ is I or F. Preferred amino acid sequences are, e.g., IEIT (SEQ ID NO:105), IRIT (SEQ ID NO:106), IQIT (SEQ ID NO:107), and IQFT (SEQ ID NO:108).

In certain embodiments, the peptide fragment comprises the amino acid sequence $X_1IX_2X_3T$ (SEQ ID NO:73), wherein $X_1$ is R or S, $X_2$ is E, R or Q, and $X_3$ is I or F. Preferred amino acid sequences are, e.g., $X_1IX_2IT$ (SEQ ID NO:74), $RIX_2IT$ (SEQ ID NO:75), $X_1IEIT$ (SEQ ID NO:76), RIEIT (SEQ ID NO:1), SIRIT (SEQ ID NO:2), SIQIT (SEQ ID NO:3), and SIQFT (SEQ. ID NO:4).

In certain embodiments, the peptide fragment comprises the amino acid sequence $PX_1IX_2X_3T$ (SEQ ID NO:77), wherein $X_1$ is R or S, $X_2$ is E, R or Q, and $X_3$ is I or F. Preferred amino acid sequences are, e.g., PRIEIT (SEQ ID NO:5), PSIRIT (SEQ ID NO:6), PSIQIT (SEQ ID NO:71) and PSIQFT (SEQ ID NO:7).

In certain embodiments, the peptide fragment comprises the amino acid sequence $X_5PX_1IX_2X_3T$ (SEQ ID NO:78), wherein $X_1$ is R or S, $X_2$ is E, R or Q, $X_3$ is I or F and $X_5$ is S or C. Preferred amino acid sequences are, e.g., SPRIEIT (SEQ ID NO:8), CPSIRIT (SEQ ID NO:9), CPSIQIT (SEQ ID NO:10) and CPSIQFT (SEQ ID NO:11).

In certain embodiments, the peptide fragment comprises the amino acid sequence $X_5PX_1IX_2X_3TX_6$ (SEQ ID NO:79), wherein $X_1$ is R or S, $X_2$ is E, R or Q, $X_3$ is I or F, $X_5$ is S or C, and $X_6$ is P or S. Preferred amino acid sequences are, e.g., SPRIEITP (SEQ ID NO:12), SPRIEITS (SEQ ID NO:13), CPSIRITS (SEQ ID NO:14), CPSIQITS (SEQ ID NO:15) and CPSIQFTS (SEQ ID NO:16).

In certain embodiments, the peptide fragment comprises the amino acid sequence $X_5PX_1IX_2X_3TX_6X_7$ (SEQ ID NO:80), wherein $X_1$ is R or S, $X_2$ is E, R or Q, $X_3$ is I or F, $X_5$ is S or C, $X_6$ is P or S, and $X_7$ is S, C or I. Preferred amino acid sequences are SPRIEITPS (SEQ ID NO:17), SPRIEITSC (SEQ ID NO:18), CPSIRITSI SEQ ID NO:19), CPSIQITSI (SEQ ID NO:20) and CPSIQFTSI (SEQ ID NO:21).

In certain embodiments, the peptide fragment comprises the amino acid sequence $X_{11}X_{10}X_9X_5PX_1IX_2X_3TX_6X_7X_8$ (SEQ ID NO:81), wherein $X_1$ is R or S, $X_2$ is E, R or Q, $X_3$ is I or F, $X_5$ is S or C, $X_6$ is P or S, $X_7$ is S, C or I, $X_8$ is H, L or S, $X_9$ is P, L or E, $X_{10}$, is G, L or F, and $X_{11}$ is S, A, V or P. Preferred amino acid sequences are, e.g., SGPSPRIEITPSH (SEQ ID NO:22), SGLSPRIEITPSH (SEQ ID NO:23), ALESPRIEITSCL (SEQ ID NO:24), VLECPSIRITSIS (SEQ ID NO:25), PFECPSIQITSIS (SEQ ID NO:26), PFECPSIQITSIS (SEQ ID NO:27) and PFECPSIQFTSIS (SEQ ID NO:28). Other preferred amino acid sequences are, e.g., KPAGASGPSPRIEITPSHELMQAGG (SEQ ID NO:29), KPAGASGLSPRIEITPSHELIQAVG (SEQ ID NO:30), PDGAPALESPRIEITSCLGLYHNNN (SEQ ID NO:31), AGGGRVLECPSIRITSISPTPEPPA (SEQ ID NO:32), LGGPKPFECPSIQITSISPNCHQEL (SEQ ID NO:33), LGGPKPFECPSIQITSISPNCHQGT (SEQ ID NO:34) and LGGPKPFECPSIQFTSISPNCQQEL (SEQ ID NO:35).

By a biologically active analog of the NFAT fragment is meant an analog that is capable of inhibiting protein-protein interaction between calcineurin and NFAT.

By analog is meant a compound that differs from the naturally occurring NFAT fragment in amino acid sequence or in ways that do not involve sequence, or both. Peptide analogs of the invention generally exhibit at least about 70% homology, preferably at least about 80% homology, more preferably at least about 90% homology, more preferably yet at least about 95% homology, more preferably yet at least about 97% homology, and most preferably at least about 98% homology, with substantially the entire sequence of a naturally occurring NFAT fragment, preferably with a segment of about 150 amino acid residues, more preferably with a segment of about 100 amino acid residues, more preferably yet with a segment of about 50 amino acid residues, more preferably yet with a segment of about 30 amino acid residues, more preferably yet with a segment of about 20 amino acid residues, more preferably yet with a segment of about 10 amino acid residues, more preferably yet with a segment of about 5 amino acid residues, and most preferably yet with a segment of about 4 amino acid residues. Non-sequence modifications include, e.g., in vivo or in vitro chemical derivatizations of the NFAT fragment. Non-sequence modifications include, e.g., changes in phosphorylation, acetylation, methylation, carboxylation, or glycosylation. Methods for making such modifications are known to those skilled in the art. For example, phosphorylation can be modified by exposing the peptide to phosphorylation-altering enzymes, e.g., kinases or phosphatases.

Preferred analogs include an NFAT fragment whose sequence differs from the wild-type sequence by one or more conservative amino acid substitutions or by one or more non-conservative amino acid substitutions, deletions, or insertions, which do not abolish biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other examples of conservative substitutions are shown in Table 1.

TABLE 1

CONSERVATIVE AMINO ACID SUBSTITUTIONS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, P-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |

TABLE 1-continued

CONSERVATIVE AMINO ACID SUBSTITUTIONS

| For Amino Acid | Code | Replace with any of |
|---|---|---|
| Phenylalanine | F | D-Phe, Tyr, D-Thr, L-Dopa, His, D-His; Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His Valine V D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., BioTechnique 1:11-15 (1989)), or saturation mutagenesis (by, e.g., chemical treatment or irradiation of single-stranded DNA in vitro, and synthesis of a complementary DNA strand; Mayers et al., Science 229:242 (1985)). Random mutagenesis can also be accomplished by, e.g., degenerate oligonucleotide generation (using, e.g., an automatic DNA synthesizer to chemically synthesize degenerate sequences; Narang, Tetrahedron 39:3 (1983); Itakura et al., Recombinant DNA, Proc. 3rd Cleveland Sympos. Macromolecules, ed. A. G. Walton, Amsterdam: Elsevier, pp. 273-289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above.

Methods for identifying desirable mutations include, e.g., alanine scanning mutagenesis (Cunningham and Wells, Science 244:1081-1085 (1989)), oligonucleotide-mediated mutagenesis (Adelman et al., DNA 2:183 (1983)), cassette mutagenesis (Wells et al., Gene 34:315 (1985)), combinatorial mutagenesis, and phage display libraries (Ladner et al., PCT International Appln. No. WO88/06630). The NFAT fragment analogs can be tested in physical and/or functional assays, e.g., in their ability to inhibit protein-protein interaction between calcineurin and NFAT, as described herein.

Other analogs within the invention include, e.g., those with modifications which increase peptide stability. Such analogs can contain, e.g., one or more non-peptide bonds (which replace the peptide bonds) in the peptide sequence. Also included are, e.g., analogs that include residues other than naturally occurring L-amino acids, e.g., D-amino acids or non-naturally occurring or synthetic amino acids, e.g., β or γ amino acids and cyclic analogs.

Analogs are also meant to include peptides in which structural modifications have been introduced into the peptide backbone so as to make the peptide non-hydrolyzable. Such peptides are particularly useful for oral administration, as they are not digested. Peptide backbone modifications include, e.g., modifications of the amide nitrogen, the α-carbon, the amide carbonyl, or the amide bond, and modifications involving extensions, deletions or backbone crosslinks. For example, the backbone can be modified by substitution of a sulfoxide for the carbonyl, by reversing the peptide bond, or by substituting a methylene for the carbonyl group. Such modifications can be made by standard procedures known to those skilled in the art. See, e.g., Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267-357, B. Weinstein (ed.), Marcel Dekker, Inc., New York (1983).

An analog is also meant to include polypeptides in which one or more of the amino acid residues include a substituent group, or polypeptides which are fused with another compound, e.g., a compound to increase the half-life of the polypeptide, e.g., polyethylene glycol.

Analogs are also meant to include those produced by introduction of amino acid substitutions, or the design of constrained peptides, cyclic peptides, and other modified peptides or analogs, where the modifications or constraints are introduced on the basis of knowledge of the conformation of the peptide bound to calcineurin, or on the basis of knowledge of the structure of a protein-protein complex formed by NFAT and calcineurin or by a fragment of NFAT (including, e.g., the 13-mer peptide described herein) and a fragment of calcineurin. The conformation of the bound peptide can be determined by techniques known to those skilled in the art, e.g., NMR, e.g., transferred nuclear Overhauser effect spectroscopy (transferred NOESY) of a rapidly dissociating peptide to determine distance constraints (Campbell and Sykes, J. Magn. Reson. 93:77-92 (1991); Lian et al., Methods Enzymol. 239:657-700 (1994)), with or without additional NMR techniques, followed by the use of the distance constraints and of constrained molecular dynamics simulations and energy minimization with available computer software (e.g., the NMR_Refine module of the InsightII™ suite of programs (Biosym/MSI, San Diego, Calif.), and the Discover™ or Discover 3.0™ molecular simulation programs (Biosym/MSI, San Diego, Calif.)) to arrive at a structural model. Alternatively, the structure of the specified complexes, including the conformation assumed by the claimed peptides in the complex, can be determined by x-ray crystallography.

Other analogs within the scope of the invention include compounds in which the peptide fragment or biologically active analog thereof is covalently linked to a ligand that binds to a site adjacent to that recognized by the 13-mer peptide described herein (See Shuker et al., Science 274: 1531-1534 (1996)), in order to produce a biologically active compound with increased affinity or specificity for the calcineurin-NFAT interaction.

The invention also includes an isolated polynucleotide encoding the peptide comprising the amino acid sequence as set forth in SEQ ID NO:73, SEQ ID NO:74, SEQ ID NO:75, SEQ ID NO:76, or biologically active analogs thereof.

The invention also includes an isolated polynucleotide encoding the peptide comprising the amino acid sequence as set forth in SEQ ID NO:105, SEQ ID NO:106, SEQ ID NO:107, SEQ ID NO:108, or biologically active analogs thereof. Preferred polynucleotide sequences are, e.g., the sequences as set forth in SEQ ID NO:109, SEQ ID NO:110, SEQ ID NO:111, SEQ ID NO:112, SEQ ID NO:113 and SEQ ID NO:114.

The invention also includes an isolated polynucleotide encoding the peptide comprising the amino acid sequence as set forth in SEQ ID NO:1, SEQ ID NO:2, SEQ ID NO:3, SEQ ID NO:4, or biologically active analogs thereof. Preferred polynucleotide sequences are, e.g., the sequences as set forth in SEQ ID NO:36, SEQ ID NO:37, SEQ ID NO:38, SEQ ID NO:39, SEQ ID NO:83 and SEQ ID NO:84.

The invention also includes an isolated polynucleotide encoding the peptide comprising the amino acid sequence as set forth in SEQ ID NO:77, SEQ ID NO:78, SEQ ID NO:79, SEQ ID NO:80, SEQ ID NO:81, or biologically active analogs thereof.

The invention also includes an isolated polynucleotide encoding the peptide comprising the amino acid sequence as set forth in SEQ ID NO:5, SEQ ID NO:6, SEQ ID NO:71, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or biologically active analogs thereof. Preferred polynucleotide sequences are, e.g., the sequences as set forth in SEQ ID NO:40, SEQ ID NO:41, SEQ ID NO:72, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:85, SEQ ID NO:86, SEQ ID NO:87, SEQ ID NO:88, SEQ ID NO:89, SEQ ID NO:90, SEQ ID NO:91 and SEQ ID NO:92.

The invention also includes an isolated polynucleotide encoding the peptide comprising the amino acid sequence as set forth in SEQ ID NO:22, SEQ ID NO:23, SEQ ID NO:24, SEQ ID NO:25, SEQ ID NO:26, SEQ ID NO:27, SEQ ID NO:28, or biologically active analogs thereof. Preferred polynucleotide sequences are, e.g., the sequences as set forth in SEQ ID NO:57, SEQ ID NO:58, SEQ ID NO:59, SEQ ID NO:60, SEQ ID NO:61, SEQ ID NO:62 and SEQ ID NO:63.

The invention also includes an isolated polynucleotide encoding the peptide comprising the amino acid sequence as set forth in SEQ ID NO:29, SEQ ID NO:30, SEQ ID NO:31, SEQ ID NO:32, SEQ ID NO:33, SEQ ID NO:34, SEQ ID NO:35, or biologically active analogs thereof. Preferred polynucleotide sequences are, e.g., sequences as set forth in SEQ ID NO:64, SEQ ID NO:65, SEQ ID NO:66, SEQ ID NO:67, SEQ ID NO:68, SEQ ID NO:69 and SEQ ID NO:70.

The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to the polynucleotides described herein, and which encode a peptide having biological activity. By percent identity is meant the maximal percent identity obtained by aligning the first base of the oligonucleotide with any base in the nucleotide sequence and then scoring the identity of aligned bases for each base in the oligonucleotide without introduction of any gaps.

The nucleotide sequences of the present invention can be in the form of, e.g., RNA, DNA or PNA, e.g., cRNA, cDNA, genomic DNA, or e.g., synthetic RNA, DNA or PNA. The nucleotide sequence can be double-stranded or single stranded, and if single stranded can be the coding strand or non-coding (anti-sense) strand.

The coding sequence which encodes the peptide fragments can be identical to the coding sequences as set forth in SEQ ID NOS:36-70, 72, 83-92 or 109-114, or can be a different coding sequence, which coding sequence, as a result of the redundancy or degeneracy of the genetic code, encodes the same peptide fragments as the nucleic acid as set forth in SEQ ID NOS:36-70, 72, 83-92 or 109-114.

The invention also includes a gene therapy vector comprising a nucleotide sequence encoding a peptide fragment of the conserved regulatory domain of NFAT protein capable of inhibiting protein-protein interaction between calcineurin and NFAT, or a biologically active analog of the peptide fragment.

By a gene therapy vector is meant a vector useful for gene therapy. Gene therapy vectors carry a gene of interest that is useful for gene therapy. The gene therapy vectors are able to be transferred to the cells of an animal, e.g., a human, and are able to express the gene of interest in such cells so as to effect gene therapy. The vector can be, e.g., chromosomal, nonchromosomal or synthetic. It can be, e.g., RNA or DNA. The vector can be, e.g., a plasmid, a virus or a phage. Preferred vectors include, e.g., retroviral vectors, adenoviral vectors, adeno-associated vectors, herpes virus vectors and Semliki Forest virus vector. A preferred retroviral vector is Murine Stem Cell Virus (MSCV), which is a variant of Moloney Murine Leukemia Virus (MoMLV).

In preferred embodiments, the gene therapy vector comprises a nucleotide sequence encoding the peptide comprising the amino acid sequence as set forth in SEQ ID NO:105, SEQ ID NO:106, SEQ ID NO:107, SEQ ID NO:108, or biologically active analogs thereof. In certain embodiments, the gene therapy vector comprises the nucleotide sequences as set forth in SEQ ID NO:109, SEQ ID NO:110, SEQ ID NO:111, SEQ ID NO:112, SEQ ID NO:113, or SEQ ID NO:114. The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to these nucleotide sequences, and which encode a peptide having biological activity.

In preferred embodiments, the gene therapy vector comprises a nucleotide sequence encoding the peptide comprising the amino acid sequence as set forth in SEQ ID NO:1, SEQ ID NO:2, SEQ ID NO:3, SEQ ID NO:4, or biologically active analogs thereof. In certain embodiments, the gene therapy vector comprises the nucleotide sequences as set forth in SEQ ID NO:36, SEQ ID NO:37, SEQ ID NO:38, SEQ ID NO:39, SEQ ID NO:83 or SEQ ID NO:84. The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to these nucleotide sequences, and which encode a peptide having biological activity. In preferred embodiments, the gene therapy vector comprises a nucleotide sequence encoding the peptide comprising the amino acid sequence as set forth in SEQ ID NO:5, SEQ ID NO:6, SEQ ID NO:71, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or biologically active analogs thereof. In certain embodiments, the gene therapy vector comprises the nucleotide sequence as set forth in SEQ ID NO:40, SEQ ID NO:41, SEQ ID NO:72, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:85, SEQ ID NO:86, SEQ ID NO:87, SEQ ID NO:88, SEQ ID NO:89, SEQ ID NO:90, SEQ ID NO:91 or SEQ ID NO:92. The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to these nucleotide sequences, and which encode a peptide having biological activity. In preferred embodiments, the gene therapy vector comprises a nucleotide sequence encoding the peptide comprising the amino acid sequence as set forth in SEQ ID NO:22, SEQ ID NO:23, SEQ ID NO:24, SEQ ID NO:25, SEQ ID NO:26, SEQ ID NO:27, SEQ ID NO:28, or biologically active analogs thereof. In certain embodiments, the gene therapy vector comprises the nucleotide sequence as set forth in SEQ ID NO:57, SEQ ID NO:58, SEQ ID NO:59, SEQ ID NO:60, SEQ ID NO:61, SEQ ID NO:62 or SEQ ID NO:63. The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to these nucleotide sequences, and which encode a peptide having biological activity.

In preferred embodiments, the gene therapy vector comprises a nucleotide sequence encoding the peptide comprising the amino acid sequence as set forth in SEQ ID NO:29, SEQ ID NO:30, SEQ NO:31, SEQ ID NO:32, SEQ ID NO:33, SEQ ID SEQ ID NO:34 and SEQ ID NO:35, or biologically active analogs thereof. In certain embodiments, the gene therapy vector comprises the nucleotide sequence as set forth in SEQ ID NO:64, SEQ ID NO:65, SEQ ID NO:66, SEQ ID NO:67, SEQ ID NO:68, SEQ ID NO:69 or SEQ ID NO:70. The invention also includes nucleotide sequences which are capable of hybridizing to and which are at least about 70%, preferably at least about 80%, more preferably yet at least about 85%, more preferably yet at least about 90%, more preferably yet at least about 95%, more preferably yet at least about 97%, and most preferably at least about 98% identical to these nucleotide sequences, and which encode a peptide having biological activity.

In certain embodiments, the gene therapy vector also has a nucleotide sequence encoding a signal peptide for effecting secretion of the NFAT peptide fragment. Examples of signal peptides include those of (pre)prolactin (Walter and Blobel, J Cell Biol 91:557-561 (1981)), apolipoprotein AI (Stoffel et al, Eur J Biochem 120:519-522 (1981)), and β-lactamase (Muller et al, J Biol Chem 257:11860-11863 (1982)). Preferably, the signal peptide is encoded 5' of the nucleotide sequence encoding the NFAT peptide fragment.

In certain embodiments, the gene therapy vector has a nucleotide sequence encoding a tag for identification of the NFAT peptide fragment. Examples of tags that can be detected with commercially available antibodies (Shiio et al, Methods Enzymol 254:497-502 (1995)) are the FLAG peptide, the peptide YPYDVPDYA (SEQ ID NO:93) from influenza virus haemagglutinin, and other peptides from T7 gene 10 protein, Myc, and bovine papillomavirus L1 protein. The sequence encoding the tag can be 5' or 3' of the nucleotide sequence encoding the NFAT peptide fragment.

In certain embodiments the gene therapy vector has a selectable marker. Examples of selectable markers include a Neomycin phosphotransferase gene, a humanized red-shifted green fluorescent protein, hygromycin resistance, puromycin resistance, luciferase, or a cell-surface protein that is recognized by a specific monoclonal antibody.

In certain embodiments, the gene therapy vector has an inducible promoter, e.g., a promoter that will allow expression of the therapeutic peptide at a specific time or in a graded manner. Such a construct is valuable, e.g., for the purpose of treating graft-versus-host disease after a transplant of bone marrow cells or stem cells genetically engineered to carry the gene therapy vector with a promoter inducible by a compound that can be administered orally; or for cell therapy of multiple sclerosis with glial cells genetically engineered to express an immunosuppressive protein or peptide in response to a cytokine or other molecule produced at a site of autoimmune demyelination.

In certain embodiments, the gene therapy vector has a cell-specific promoter to allow inhibition of the calcineurin-NFAT interaction in one cell type, without disturbing normal NFAT function in other types of cells.

The invention also includes a cell having a gene therapy vector described herein. Preferably, the cell is an animal cell. The gene therapy vectors described herein can be introduced into a cell, e.g., by transformation, transfection, transduction, infection, or ex vivo injection. Preferably, they are targeted to a particular cell type or cell.

The invention also includes a method for producing a peptide capable of inhibiting protein-protein interaction between calcineurin and NFAT, comprising culturing a cell having a gene therapy vector described herein under conditions that permit expression of the peptide.

The invention also includes a method for treating an immunorelated disease or condition in an animal. Immune-related diseases or conditions include, e.g., acute immune diseases, chronic immune diseases and autoimmune diseases. It is also meant to include treatment of tissue or organ transplant graft rejections or graft-versus-host disease. A gene therapy vector described herein is administered to the animal.

The invention also includes a method for providing an animal having an immune-related disease or condition with a therapeutically effective level of a peptide capable of inhibiting protein-protein interaction between calcineurin and NFAT. A gene therapy vector described herein is administered to the animal.

The invention also includes a method for inhibiting an immune response in an animal. An animal in need of inhibition of an immune response is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered to the animal so as to inhibit the immune response in the animal.

The peptide fragment can be any of the peptide fragments of the conserved regulatory domain of NFAT protein of this invention described herein. Certain preferred peptide fragments comprise the amino acid sequence $X_1IX_2X_3T$ (SEQ ID NO:73) or a biologically active analog thereof, wherein $X_1$ is R or S, $X_2$ is E, R or Q, and $X_3$ is I or F. In certain embodiments, the peptide fragment comprises the amino acid sequence as set forth in SEQ ID NO:1, SEQ ID NO:2, SEQ ID NO:3, SEQ ID NO:4, or biologically active analogs thereof.

Other preferred peptide fragments comprise the amino acid sequence $IX_2X_3T$ (SEQ ID NO:104) or a biologically active analog thereof, wherein $X_2$ is E, R or Q, and $X_3$ is I or F. In certain embodiments, the peptide fragment comprises the amino acid sequence as set forth in SEQ ID NO:105, SEQ ID NO:106, SEQ ID NO:107, SEQ ID NO:108, or biologically active analogs thereof.

In certain embodiments, the therapeutically effective amount of the peptide fragment is provided by providing to the animal a recombinant nucleic acid having a nucleotide sequence encoding the peptide fragment or a biologically active analog thereof, and which is capable of expressing the peptide fragment or biologically active analog thereof in vivo. The peptide fragment is administered to the animal by administering the recombinant nucleic acid. The nucleic acid can be, e.g., any of the polynucleotides described herein. Certain preferred nucleic acids are polynucleotides encoding the peptide comprising the amino acid sequence as set forth in SEQ ID NO:1, SEQ ID NO:2, SEQ ID NO:3, SEQ ID NO:4 or biologically active analogs thereof, e.g., the sequences as set forth in SEQ ID NO:36, SEQ ID NO:37, SEQ ID NO:38 and SEQ ID NO:39. Other preferred nucleic acids are polynucleotides encoding the peptide comprising the amino acid sequence as set forth in SEQ ID NO:105, SEQ ID NO:106, SEQ ID NO:107, SEQ ID NO:108, or biologically active analogs thereof, e.g., the sequences as set forth in SEQ ID NO:109, SEQ ID NO:110, SEQ ID NO:111, SEQ ID NO:112, SEQ ID NO:113, and SEQ ID NO:114. In certain embodiments, the recombinant nucleic acid is a gene therapy vector, e.g., as described herein.

In certain embodiments, the therapeutically effective amount of the peptide fragment is provided by providing to the animal a composition comprising animal cells wherein a recombinant nucleic acid having a nucleotide sequence encoding the peptide fragment has been introduced ex vivo into the animal cells so as to express the peptide fragment in the animal cells. The peptide fragment is administered to the animal by administering the animal cells having the recombinant nucleic acid. Preferably, the recombinant nucleic acid is a gene therapy vector, e.g., as described herein. Preferably, the animal cells are derived from the animal to be treated or allogeneic cells.

Administration of an agent, e.g., a peptide or nucleic acid can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

In certain embodiments of the invention, the administration can be designed so as to result in sequential exposures to the agent over some time period, e.g., hours, days, weeks, months or years. This can be accomplished by repeated administrations of the agent, e.g., by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants. Examples of systems in which release occurs in bursts include, e.g., systems in which the agent is entrapped in liposomes which are encapsulated in a polymer matrix, the liposomes being sensitive to a specific stimulus, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be administered prior to or subsequent to the appearance of disease symptoms. In certain embodiments, the agent is administered to patients with familial histories of the disease, or who have phenotypes that may indicate a predisposition to the disease, or who have been diagnosed as having a genotype which predisposes the patient to the disease, or who have other risk factors.

The agent is administered to the animal in a therapeutically effective amount. By therapeutically effective amount is meant that amount which is capable of at least partially preventing or reversing the disease. A therapeutically effective amount can be determined on an individual basis and will be based, at least in part, on consideration of the species of animal, the animal's size, the animal's age, the efficacy of the particular agent used, the longevity of the particular agent used, the type of delivery system used, the time of administration relative to the onset of disease symptoms, and whether a single, multiple, or controlled release dose regimen is employed. A therapeutically effective amount can be determined by one of ordinary skill in the art employing such factors and using no more than routine experimentation.

In certain preferred embodiments, the concentration of the agent if it is a peptide is at a dose of about 0.1 to about 1000 mg/kg body weight/day, more preferably at about 0.1 to about 500 mg/kg/day, more preferably yet at about 0.1 to about 100 mg/kg/day, and most preferably at about 0.1 to about 5 mg/kg/day. Preferably, the dosage form is such that it does not substantially deleteriously affect the animal.

In certain embodiments, a therapeutically effective amount of an agent which is a peptide can be administered by providing to the animal a nucleic acid encoding the peptide and expressing the peptide in vivo. Preferably, the dosage form is such that it does not substantially deleteriously affect the animal. Nucleic acids encoding the peptide can be administered in any biologically effective carrier, e.g. any formulation or composition capable of effectively delivering the nucleotide sequence for the peptide to cells in vivo. Approaches include, e.g., insertion of the nucleic acid into viral vectors, including, e.g., retrovirus, adenovirus, adeno-associated virus, herpes virus and Semliki Forest virus vectors. Viral vectors can be delivered to the cells, e.g., by infection or transduction using the virus. Viral vectors can also be delivered to the cells, e.g., by physical means, e.g., by electroporation, lipids, cationic lipids, liposomes, DNA gun, $Ca_3(PO_4)_2$ precipitation, or delivery of naked DNA. In certain preferred embodiments, the virus is administered by injection, e.g., intramuscular injection, in a dose range of about $10^3$ to about $10^{10}$ infectious particles per injection per treatment, more preferably in a dose range of about $10^5$ to about $10^8$ infectious particles per injection per treatment. Single or multiple doses can be administered over a given period of time, depending, e.g., upon the disease. An alternative is insertion of the nucleic acid encoding the peptide into a bacterial or eukaryotic plasmid. Plasmid DNA can be delivered to cells with the help of, e.g., cationic liposomes (Lipofectin™; Life Technologies, Inc., Gaithersburg, Md.) or derivatized (e.g., antibody conjugated) polylysine conjugates, gramicidin S, streptolysin artificial viral envelopes or other such carriers or delivery aids, as well as direct injection of the gene construct or $Ca_3(PO_4)_2$ precipitation carried out in vivo, or by use of a gene gun. The above-described methods are known to those skilled in the art and can be performed without undue experimentation.

In certain embodiments, the nucleic acid is administered to the animal by introducing ex vivo the nucleic acid into cells of the animal or allogeneic cells, and administering the cells having the nucleic acid to the animal. Any cell type can be used. In certain embodiments, the cells having the introduced nucleic acid are expanded and/or selected after the nucleic acid transfer. The cells having the transferred nucleic acid are subsequently administered to the animal. Preferably, the cells are administered to the animal in a dose range of about $1 \times 10^6$ to about $1 \times 10^9$ cells/dosage/treatment, and most preferably at about $1 \times 10^7$ to about $1 \times 10^8$ cells/dosage/treatment. The cells can be administered by any method which results in delivering the transferred nucleic acid in the cells to the desired target. For example, the cells can be implanted directly into a specific tissue of the animal, or implanted after encapsulation within an artificial polymer matrix. Examples of sites of implantation include the lungs or airways, skin, conjunctiva, central nervous system, peripheral nerve, a grafted kidney, or an inflamed joint.

Choice of the particular delivery system will depend on such factors as the intended target and the route of administration, e.g., locally or systemically. Targets for delivery of the agent can be, e.g., specific target cells which are causing or contributing to disease. For example, the target can be resident or infiltrating cells in the lungs or airways that are contributing to an asthmatic illness; resident or infiltrating cells in the nervous system that are contributing to demyelinating disease; resident or infiltrating cells responsible for rejection of a kidney graft; grafted cells whose activation produces graft-versus-host disease; or resident or infiltrating cells whose activation underlies inflammation or arthritic degeneration of a joint. Administration can be directed to one or more cell types, and to one or more subsets of cells within a cell type, so as to be therapeutically effective, by methods known to those skilled in the art. For example, the agent can be coupled to an antibody, to a ligand to a cell surface receptor, or to a toxin component, or can be contained in a particle which is selectively internalized into cells, e.g., liposomes, or a virus where the viral receptor binds specifically to a certain cell type, or a viral particle lacking the viral nucleic acid, or can be administered by local injection. In certain embodiments, administration is done in a prenatal animal or embryonic cell.

In certain embodiments, other therapy is additionally administered. For example, another therapeutic agent, chemotherapy, radiation or surgery, is additionally administered to the animal, either simultaneously or at different times.

The invention also includes a method for treating a disease involving hyperactivity or inappropriate activity of the immune system, a transplant graft rejection, or graft-versus-host disease in an animal. An animal in need of treatment for a disease involving hyperactivity or inappropriate activity of the immune system, a transplant graft rejection, or graft-versus-host disease, is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered to the animal in a therapeutically effective amount such that treatment of the disease involving hyperactivity or inappropriate activity of the immune system, transplant graft rejection, or graft-versus-host disease, occurs.

Immune system diseases involving hyperactivity or inappropriate activity of the immune system include, e.g., acute immune diseases, chronic immune diseases and autoimmune diseases. Examples of such diseases include rheumatoid arthritis, inflammatory bowel disease, allogeneic or xenogeneic transplantation (organ, bone marrow, stem cells, other cells and tissues), graft-versus-host disease, aplastic anemia, psoriasis, lupus erytematosus, inflammatory disease, type I diabetes, asthma, pulmonary fibrosis, scleroderma, dermatomyositis, Sjogren's syndrome, postpericardiotomy syndrome, Kawasaki disease, Hashimoto's thyroiditis, Graves' disease, myasthenia gravis, pemphigus vulgaris, autoimmune hemolytic anemia, idiopathic thrombopenia, chronic glomerulonephritis, Goodpasture's syndrome, Wegner's granulomatosis, multiple sclerosis, cystic fibrosis, chronic relapsing hepatitis, primary biliary cirrhosis, uveitis, allergic rhinitis, allergic conjunctivitis, atopic dermatitis and autoimmune thyroiditis. Transplant graft rejections can result from tissue or organ transplants. Graft-versus-host disease can result from bone marrow or stem cell transplantation.

Treating is meant to include, e.g., preventing, treating, reducing the symptoms of, or curing the disease or condition. In certain embodiments, the therapeutically effective amount of the peptide fragment or biologically active analog thereof is administered by providing to the animal a nucleic acid encoding the peptide fragment or biologically active analog thereof, and expressing the peptide fragment or biologically active analog thereof in vivo.

The invention also includes a method for treating an animal at risk for a disease involving hyperactivity or inappropriate activity of the immune system, a transplant graft rejection, or graft-versus-host disease. An animal at risk for a disease involving hyperactivity or inappropriate activity of the immune system, a transplant graft rejection, or graft-versus-host disease, is provided. A therapeutically effective amount of a peptide fragment of the conserved regulatory domain of NFAT protein capable of inhibiting protein-protein interaction between calcineurin and NFAT, or a biologically active analog thereof, is provided. The peptide fragment or biologically active analog thereof is administered in a therapeutically effective amount such that treatment occurs.

Being at risk for the disease can result from, e.g., a family history of the disease, a genotype which predisposes to the disease, or phenotypic symptoms which predispose to the disease.

The invention also includes a method for gene therapy. An animal cell is genetically modified such that it is able to express a peptide fragment or biologically active analog thereof of the conserved regulatory domain of NFAT protein, the peptide fragment being capable of inhibiting calcineurin-mediated NFAT activation, so as to effect gene therapy. In certain embodiments, the animal cells are genetically modified by introducing into the cells a recombinant nucleic acid having a nucleotide sequence encoding the peptide fragment and which is capable of expressing the peptide fragment in vivo. Preferably, the recombinant nucleic acid is a gene therapy vector, e.g., as described herein.

The invention also includes a pharmaceutical composition for treating an immune-related disease or condition in an animal comprising a therapeutically effective amount of a peptide fragment of the conserved regulatory domain of NFAT protein capable of inhibiting protein-protein interaction between calcineurin and NFAT, or a biologically active analog thereof, and a pharmaceutically acceptable carrier. The peptide fragment can be, e.g., any of the peptide fragments described herein. Pharmaceutically acceptable carriers include, e.g., water, saline, dextrose, glycerol, ethanol, liposomes and lipid emulsions.

The invention also includes a pharmaceutical composition for treating an immune-related disease or condition in an animal, comprising a therapeutically effective amount of a recombinant nucleic acid having a nucleotide sequence encoding a peptide fragment of the conserved regulatory domain of NFAT protein capable of inhibiting protein-protein interaction between calcineurin and NFAT, or a biologically active analog thereof, and a pharmaceutically acceptable carrier. The nucleic acid can be, e.g., any of the polynucleotides described herein.

The invention also includes a pharmaceutical composition for treating an immune-related disease or condition in an animal, comprising a therapeutically effective amount of animal cells wherein a recombinant nucleic acid having a nucleotide sequence encoding a peptide fragment of the conserved regulatory domain of NFAT protein capable of inhibiting protein-protein interaction between calcineurin and NFAT, or a biologically active analog thereof, has been introduced into the animal cells so as to express the peptide fragment; and a pharmaceutically acceptable carrier. Preferably, the animal cells are cells derived from the animal to be treated or allogeneic cells.

The invention also includes a method for inhibiting protein-protein interaction between calcineurin and NFAT in vivo. A cell having calcineurin and NFAT is provided. A peptide fragment or a biologically active analog thereof of the conserved regulatory domain of NFAT protein capable of inhibiting protein-protein interaction between calcineurin and NFAT is provided. The calcineurin and peptide fragment or biologically active analog thereof are contacted in vivo such that protein-protein interaction between the calcineurin and the NFAT is inhibited.

The invention also includes a method for inhibiting protein-protein interaction between calcineurin and NFAT in vitro. Calcineurin and NFAT are provided. A peptide fragment or a biologically active analog thereof of the conserved regulatory domain of NFAT protein capable of inhibiting protein-protein interaction between calcineurin and NFAT is provided. The calcineurin and peptide fragment or biologically active analog thereof are contacted b vitro such that protein-protein interaction between the calcineurin and the NFAT is inhibited.

The invention also includes a method for evaluating an agent for use in modulating an immune response. A cell is provided. An agent, e.g., a peptide fragment of the conserved regulatory domain of NFAT protein or biologically active analogs thereof, is provided. The effect of the agent on an aspect of calcineurin mediated NFAT activation is evaluated. A change in the aspect of calcineurin-mediated NFAT activation is indicative of the usefulness of the agent in modulating an immune response.

Any aspect of calcineurin-mediated NFAT activation can be evaluated, e.g., protein-protein interaction between calcineurin and NFAT, dephosphorylation of NFAT by calcineurin, recruitment of NFAT to the nucleus in a cell, conformational change in NFAT, or activation of NFAT-dependent gene transcription.

The invention also includes a method for high throughput screening of candidate agents to identify an agent that inhibits protein-protein interaction between calcineurin and NFAT. A first compound is provided. The first compound is calcineurin or a biologically active derivative thereof, or the first compound is NFAT or a biologically active derivative thereof. A second compound is provided which is different from the first compound and which is labeled. The second compound is calcineurin or a biologically active derivative thereof, or the second compound is NFAT or a biologically active derivative thereof. A candidate agent is provided. The first compound, second compound and candidate agent are contacted with each other. The amount of label bound to the first compound is determined. A reduction in protein-protein interaction between the first compound and the second compound as assessed by label bound is indicative of the usefulness of the agent in inhibiting protein-protein interaction between calcineurin and NFAT. Preferably, the reduction is assessed relative to the same reaction without addition of the candidate agent.

In certain embodiments, the first compound which is provided is attached to a solid support. Solid supports include, e.g., resins, e.g., agarose and a multiwell plate. In certain embodiments, the method includes a washing step after the contacting step, so as to separate bound and unbound label.

By high-throughput screening is meant that the method can be used to screen a large number of candidate agents easily and quickly. In preferred embodiments, a plurality of candidate agents are contacted with the first compound and second compound. The different candidate agents can be contacted with the other compounds in groups or separately. Preferably, each of the candidate agents is contacted with both the first compound and the second compound in separate wells. For example, the method can screen libraries of potential agents. Libraries are meant to include, e.g., natural product libraries, organic chemical libraries, combinatorial chemical libraries, peptide libraries, and modified peptide libraries, including, e.g., D-amino acids, unconventional amino acids, or N-substituted amino acids. Preferably, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

Calcineurin and biologically active derivatives thereof is meant to include, e.g., intact calcineurin; calcineurin A chain; fragments of calcineurin that are biologically active in binding NFAT, e.g., a catalytic domain fragment of the calcineurin A chain that binds to NFAT; analogs of calcineurin or a calcineurin fragment that are biologically active in binding NFAT; and chimeric recombinant proteins, e.g., calcineurin or a biologically active fragment of calcineurin fused to another peptide or protein such that calcineurin retains its NFAT-binding activity. The calcineurin and its biologically active derivatives can be natural, recombinant or synthesized. In certain preferred embodiments, the calcineurin can be from, e.g., a mammal, e.g., a human, or yeast. Calcineurin can be obtained, e.g., in cell extracts of cells that normally express calcineurin, or by expressing recombinant calcineurin protein in eukaryotic or prokaryotic cells. In certain embodiments, calmodulin is included in the assay so as to confer calcium responsiveness on calcineurin.

NFAT and biologically active derivatives thereof is meant to include intact NFAT, e.g., NFAT1, NFAT2, NFAT3 or NFAT4; fragments of NFAT that are biologically active, e.g., that retain the ability to form a protein-protein interaction with calcineurin or the ability of inhibiting the binding of NFAT to calcineurin, e.g., a peptide fragment of the conserved regulatory domain of NFAT, as described herein; analogs of NFAT or an NFAT fragment that are biologically active; and chimeric recombinant proteins, e.g., NFAT or a biologically active fragment of NFAT fused to another peptide or protein such that NFAT retains its activity. Examples of such chimeric recombinant proteins include: (i) NFAT fused to maltose-binding protein or glutathione S-transferase (GST) so as to immobilize the NFAT on a solid support, e.g., a resin; (ii) NFAT fused to green fluorescent protein or one of its variants for use in a fluorescence assay or a fluorescence energy transfer assay; and (iii) NFAT fused to a peptide tag so as to allow its recognition by a specific antibody or its labeling by a specific protein kinase. The NFAT and its biologically active derivatives can be natural, recombinant or synthesized. NFAT can be, e.g., a mammalian protein, e.g., human or murine. NFAT can be obtained, e.g., in cell extracts of cells that normally express NFAT, or by expressing a recombinant NFAT protein in eukaryotic or prokaryotic cells.

In certain embodiments, the NFAT derivative is a mutated NFAT that has increased affinity for calcineurin. Such mutants are obtained, e.g., by applying a two-hybrid screen to mutagenized NFAT (see, e.g., Mendelsohn and Brent, Curr. Opin. Biotech. 5:482-486 (1994); Goldfarb et al, J Biol Chem 271:2683-2688 (1996); Colas et al, Nature 380:548-550 (1996)) or using any other selection or screening method known to those skilled in the art, or produced by introducing into NFAT amino acid substitutions identified through screening peptide libraries or phage display libraries (see, e.g., Kast and Hilvert, Curr. Opin. Struct. Biol. 7:470-479 (1997)). Advantages of using mutant NFAT proteins that bind calcineurin with higher affinity are reducing the amount of radiolabeled calcineurin required for an assay, permitting more stringent washing, and expanding the range of assays that produce a detectable signal.

In certain embodiments, the first compound is calcineurin or a biologically active derivative thereof, and the second compound is NFAT or a biologically active derivative thereof. In other embodiments, the first compound is NFAT or a biologically active derivative thereof, and the second compound is calcineurin or a biologically active derivative thereof. The solid support to which the first compound is attached includes, e.g., Sepharose beads, SPA beads and a multiwell plate. Preferably, SPA beads (microspheres that incorporate a scintillant) are used when the assay is performed without a washing step, e.g., in a scintillation proximity assay. Preferably, Sepharose beads are used when the assay is performed with a washing step. The second compound can be labeled with any label that will allow its detection, e.g., a radiolabel, a fluorescent agent, biotin, a peptide tag, or an enzyme fragment. Preferably, the second compound is radiolabeled, e.g., with $^{125}$I or $^{3}$H.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. Methods based on surface plasmon resonance, as, e.g., in the BIAcore biosensor (Pharmacia Biosensor, Uppsala, Sweden) or evanescent wave excitation of fluorescence are particularly suited to measure recruitment of, e.g., NFAT (or fluorescently labeled NFAT) to a surface on which calcineurin is immobilized. In certain other embodiments, the interaction of NFAT and calcineurin is detected by fluorescence resonance energy transfer (FRET) between a donor fluorophore covalently linked to NFAT (e.g., a fluorescent group chemically conjugated to NFAT, or a variant of green fluorescent protein (GFP) expressed as an NFAT-GFP chimeric protein) and an acceptor fluorophore covalently linked to calcineurin, where there is suitable overlap of the donor emission spectrum and the acceptor excitation spectrum to give efficient nonradiative energy transfer when the fluorophores are brought into close proximity through the protein-protein interaction of NFAT and calcineurin.

In certain embodiments, the protein-protein interaction is detected by reconstituting domains of an enzyme, e.g., p-galactosidase (see Rossi et al, Proc. Natl. Acad. Sci. USA 94:8405-8410 (1997)). The detection method used is appropriate for the particular enzymatic reaction, e.g., by chemiluminescence with Galacton Plus substrate from the Galacto-Light Plus assay kit (Tropix, Bedford, Mass.) or by fluorescence with fluorescein di-β-D-galactopyranoside (Molecular Probes, Eugene, Oreg.) for β-galactosidase. Competition of the protein-protein interaction by the candidate agents or by the 13-mer or 26-mer inhibitory peptides described herein, is evident in a reduction of the measured enzyme activity. This assay can be performed with proteins in vitro or in vivo. An advantage of this embodiment in vivo is that only compounds sufficiently permeable through the membrane of living cells will be scored positive, and thus agents most likely to reach effective concentrations within cells when administered therapeutically can be identified. Measurement of reconstituted S-galactosidase activity in living cells has been demonstrated with fluorescein di-β-D-galactopyranoside (Molecular Probes, Eugene, Oreg.) as substrate. See Rossi et al., Proc. Natl. Acad. Sci. USA 94:8405-8410 (1997).

In certain embodiments, the protein-protein interaction is assessed by fluorescence ratio imaging (Bacskai et al, Science 260:222-226 (1993)) of suitable chimeric constructs of NFAT and calcineurin in cells, or by variants of the two-hybrid assay (Fearon et al, Proc Natl Acad Sci USA 89:7958-7962 (1992); Takacs et al, Proc Natl Acad Sci USA 90:10375-10379 (1993); Vidal et al, Proc Natl Acad Sci USA 93:10315-10320 (1996); Vidal et al, Proc Natl Acad Sci USA 93:10321-10326 (1996)) employing suitable constructs of NFAT and calcineurin and tailored for a high throughput assay to detect compounds that inhibit the NFAT calcineurin interaction. These embodiments have the advantage that the cell permeability of compounds that act as specific inhibitors in the assay is assured.

Any false positives identified in these assays, such as protein denaturants or natural product samples contaminated with a protease activity, can be detected and eliminated through secondary assays that demonstrate that their inhibitory action is nonspecific, e.g., that such compounds interfere with known protein-protein interactions between pairs of proteins unrelated to NFAT and calcineurin.

The invention also includes a method for high-throughput screening of candidate agents to identify an agent that inhibits dephosphorylation of NFAT by calcineurin. Phosphorylated NFAT is provided. Calcineurin or a biologically active derivative thereof having enzymatic activity is provided. A candidate agent is provided. The phosphorylated NFAT, the calcineurin or biologically active derivative thereof, and the candidate agent are contacted with each other in reaction media, e.g., buffer, under conditions that allow enzymatic activity of calcineurin. In certain embodiments, the NFAT is separated from the reaction media. It is determined whether phosphate remains associated with the NFAT. If phosphate remains associated is indicative of the usefulness of the agent in dephosphorylation of NFAT by calcineurin.

In certain embodiments, the phosphorylated with the NFAT, it inhibiting NFAT is labeled. The phosphate can be labeled with any label that will allow its detection. Preferably, the phosphate is radiolabeled, e.g., with $^{32}$P or $^{33}$P. In certain embodiments, determination of whether phosphate remains associated with the NFAT is accomplished by determining the release of labeled phosphate in the reaction media, or the retention of labeled phosphate on the NFAT. A reduction in release of labeled phosphate from the NFAT by the calcineurin, or an increase in retention of labeled phosphate on the NFAT, is indicative of the usefulness of the agent in inhibiting dephosphorylation of NFAT by calcineurin. Preferably, the reduction is assessed relative to the same reaction without addition of the candidate agent.

In certain embodiments, the phosphorylated NFAT that is provided is attached to a solid support.

In preferred embodiments, a plurality of candidate agents are contacted with the phosphorylated NFAT which optionally is attached to a solid support, and the calcineurin or biologically active derivative thereof. The different candidate agents can be contacted with the NFAT and calcineurin in groups or separately. Preferably, each of the candidate agents is contacted with the NFAT and the calcineurin in separate wells.

NFAT in its phosphorylated form can be obtained by any method known to those skilled in the art. Methods that involve enzymatic labeling using a protein kinase in vitro are preferred where $^{32}$P is incorporated, since high specific activities can be achieved. ERK2 phosphorylates GST-NFAT1 fusion protein on sites accessible to calcineurin. A combination of protein kinase A (protein kinase, catalytic subunit; Sigma Chemical Co., St. Louis, Mo.) and glycogen synthase kinase 3β (New England Biolabs, Beverly, Mass.) phosphorylates GST-NFAT2 on a set of sites that correspond to those phosphorylated b vivo (Beals et al, Science 275:1930-1933 (1997)). For assays that measure $^{32}$P-phosphate remaining covalently associated with the protein after the incubation with calcineurin, the background signal due to phosphate incorporated at calcineurin-insensitive sites may be lowered by preblocking all substrate sites for the kinase in a reaction with unlabeled-ATP, treating with calcineurin, washing, and then incorporating $^{32}$P in a second kinase reaction that labels predominantly those sites that are accessible to calcineurin.

For assays that use nonradioactive phosphorylated NFAT or $^{32}$P labeled NFAT in native form, mammalian cells or insect cells expressing high levels of recombinant protein after transformation with a baculovirus vector can be used to obtain sufficient NFAT in phosphorylated form. A method for preparation of fully phosphorylated native NFAT1 from mammalian cells is described in Shaw et al., Proc. Natl. Acad. Sci. USA 92:11205-11209 (1995). Fully phosphorylated NFAT1 can also be obtained by lysis of the cells in a detergent-containing buffer, provided that sufficient concentrations of phosphatase inhibitors, e.g., 60 mM sodium pyrophosphate, 10 mM EDTA, and 5 mM EGTA, are included in the lysis buffer. Since the inhibitors are subsequently washed away after NFAT is purified away from endogenous phosphatases, their inclusion at the lysis step does not compromise a subsequent enzymatic assay using calcineurin. Minor modifications of these procedures that may be necessary for isolation of phosphorylated NFAT from insect cells include, e.g., use of additional protease inhibitors, additional phosphatase inhibitors, or higher concentrations of the inhibitors. The NFAT expression construct introduced into these cells in a baculovirus vector preferably encodes a chimeric protein including an epitope tag or hexahistidine tag, or a fusion protein with glutathione S transferase, or some similar fusion protein providing for facile purification of the expressed protein. In some cases, phosphorylated NFAT or $^{32}$P-labeled NFAT can be obtained by coexpression of NFAT and a constitutively active kinase in bacteria, e.g., in E. coli.

In certain embodiments, determining dephosphorylation of NFAT can be accomplished by examining specific sites remaining phosphorylated in the NFAT protein after treatment with calcineurin. A compound is scored as positive if it increases the retention of covalently bound phosphate on a specific site or sites of NFAT. Preferably, the presence or absence of covalently bound phosphate is determined using antibodies, or a functionally equivalent reagent, e.g., genetically engineered antibodies, minibodies or aptamers, that discriminate between phosphorylated and unphosphorylated forms of a specific peptide in the context of the larger protein or protein fragment. NFAT peptides that can be used include, e.g., FQNIPAHYSPRT (SEQ ID NO:94), PAHYSPRTSPIM (SEQ ID NO:95), or SPRTSPIMSPRT (SEQ ID NO:96) (from the sequence FQNIPAHYSPRTSPIMSPRT (SEQ ID NO:97), residues 207 to 226 in murine NFAT1) or PVPRPASRSSSP (SEQ ID NO:98), RPASRSSSPG (SEQ ID NO:99), or ASRSSSPGAKRR (SEQ ID NO:100)(from the sequence PVPRPASRSSSPGAKRR (SEQ ID NO:101), residues 239 to 255 in murine NFAT1). Antibodies to phosphorylated or dephosphorylated NFAT peptides can be raised, e.g., by immunization of rabbits. See e.g., Czernik et al, Methods Enzymol 201:264-283 (1991) for preparation and characterization of serum or monoclonal antibodies using short synthetic peptides (10-12 residues) corresponding to the sequence surrounding a phosphorylation site. The unphosphorylated peptides can be obtained by conventional methods of chemical synthesis, e.g., Merrifield solid phase synthesis. The phosphopeptides can be obtained, e.g., by in vitro phosphorylation of the synthetic peptides with kinase in instances where the synthetic peptide includes flanking residues that form a consensus site for the kinase (Czernik et al, Methods Enzymol 201:264-283 (1991)), or, e.g., by chemical synthesis of peptides phosphorylated on serine or threonine residues (Perich J W, Methods Enzymol 201:225-233 (1991)). The antisera or monoclonal antibodies can be tested to determine whether they show the ability to discriminate between phosphorylated and unphosphorylated peptides, e.g., by dot immunoblotting or by ELISA (Czernik et al, Methods Enzymol 201:264-283 (1991)). To ensure that a specific antiserum or monoclonal antibody reagent discriminates between phosphopeptide and dephosphopeptide in the context of NFAT protein, and to select a high-affinity reagent with low background signal in the high-throughput screening assay, the candidate antiserum or monoclonal antibody can be further tested under the conditions to be used in the high-throughput screening assay.

Any antibody based assay can be used. Preferably, an automated assay that reflects the relative amount of phosphorylated or unphosphorylated peptide is used. For example, a very efficient method of monitoring dephosphorylation is to use fluorescence resonance energy transfer between two appropriately labeled antibodies to two distinct phosphopeptides, capable of simultaneous binding to the protein, which are added directly to the reaction after stopping the phosphatase incubation with, e.g., EGTA, another inhibitor of calcineurin activity, or by mild protein denaturation. Variants of this embodiment include, e.g., antibodies directed against the dephosphorylated forms of two distinct NFAT peptides, corresponding miniaturized antibodies ("minibodies"; Tramontano et al, J. Mol. Recognit. 7:9-24 (1994); Martin et al, EMBO J. 13:5303-5309 (1994); Martin et al, J. Mol. Biol 255:86-97 (1996)), or peptide aptamers (Colas et al, Nature 380:548-550 (1996)) selected to recognize phosphorylated or dephosphorylated forms of NFAT peptides. In some variants of this embodiment, a single fluorescently labeled antibody, minibody, or peptide aptamer that binds to a phosphorylated or dephosphorylated form of an NFAT peptide is paired with fluorescently tagged NFAT in a fluorescence resonance energy transfer assay; or a fluorescently labeled antibody, minibody, or peptide aptamer directed to a phosphopeptide or dephosphopeptide is paired in a fluorescence resonance energy transfer assay with a second labeled antibody, minibody, or peptide aptamer that binds constitutively to NFAT or a peptide tag at a site unaffected by phosphorylation or dephosphorylation of the protein. In embodiments in which the antibodies, minibodies, or peptide aptamers are continuously present during the incubation with calcineurin, the reagents preferably are directed against the dephosphopeptide so that they will not interfere with access of calcineurin to the phosphopeptide.

In certain embodiments, the screening assay uses measurements of release of $^{32}P$ from a reporter site introduced into recombinant NFAT, or measurements with antibodies to the phosphorylated or dephosphorylated forms of a reporter site introduced into recombinant NFAT. The inserted reporter site takes the form of a short peptide sequence, known to be an efficient substrate for a specific protein kinase, that is genetically engineered into NFAT. The inserted site that is used is able to be phosphorylated efficiently in vitro in its context within the NFAT protein, the phosphorylated site is dephosphorylated by calcineurin, and the efficiency of dephosphorylation is reduced by a 13-mer or 25-mer inhibitory peptide described herein, showing that the specific protein-protein recognition of NFAT by calcineurin is essential for dephosphorylation.

In certain embodiments, the interaction of NFAT with the enzyme active site of calcineurin, as distinct from the recognition site where the protein-protein interaction is disrupted by a 13-mer or 25-mer inhibitory peptide described herein, is assessed by examining the activity of calcineurin against a second substrate in the presence of NFAT. Because binding of NFAT to the recognition site brings substrate peptides within NFAT into proximity of the active site, and indeed into the active site as evidenced by their consequent dephosphorylation, NFAT exhibits competition with other substrates that are dephosphorylated by calcineurin. In the absence of binding to the recognition site, NFAT may still compete with other substrates, but only at significantly higher concentrations. Since the agents sought in this assay, like the 13-mer peptide, do not inhibit calcineurin activity against substrates other than NFAT, their presence in the assay will reduce competition by NFAT and cause an apparent stimulation of calcineurin activity against the assayed substrate.

Such an assay uses a standard calcineurin phosphatase assay. The concentration of NFAT required for competition depends on many factors, e.g., the substrate, assay time, temperature and assay buffer, which are determined for particular reaction conditions by simple testing of a range of NFAT concentrations in pilot experiments. The control reaction that shows the dependence of the competition on NFAT-calcineurin recognition is carried out with inclusion of a 13-mer or 25-mer inhibitory peptide described herein. In one embodiment, the measurement of calcineurin phosphatase activity is made by determining the release of $^{32}P$ from a phosphopeptide substrate, e.g., $^{32}P$-RII peptide. In another embodiment, the enzymatic activity of calcineurin is determined by use of a biotinylated phosphopeptide substrate that can be captured, subsequent to the incubation with calcineurin, on a streptavidin-coated solid support and probed with an antibody specific for the dephosphopeptide. In certain embodiments, detection is by formation of a fluorescent product with, e.g., 4-nitrophenylphosphate (Molecular Probes, Eugene, Oreg.) or fluorescein diphosphate (Molecular Probes, Eugene, Oreg.) as substrate. Those skilled in the art are aware of many alternative ways to assess the enzymatic activity of calcineurin. An advantage of this embodiment is that such assays do not require phosphorylated NFAT.

In any of the dephosphorylation assays described herein, agents that inhibit NFAT dephosphorylation by preventing the specific interaction between calcineurin and NFAT are identified, as well as agents that act by a different mechanism, e.g., as general inhibitors of calcineurin. The latter general inhibitors can be eliminated, e.g., by a second screening assay which tests the agent's ability to inhibit dephosphorylation of other known substrates of calcineurin. The assay based on competition with a second substrate may identify general activators of calcineurin, which can likewise be eliminated, e.g., in a second screening assay that tests the agent's ability to augment dephosphorylation of the second substrate when the incubation is performed in the absence of NFAT. Further, to confirm that the mechanism of action is interference with the protein-protein interaction of NFAT and calcineurin, all compounds identified in the dephosphorylation assay can, e.g., be tested directly for their interference in the protein-protein interaction of NFAT and calcineurin using the assays described herein.

The invention also includes a method for high-throughput screening of candidate agents to identify an agent that inhibits conformational change in NFAT from dephosphorylation by calcineurin. Phosphorylated NFAT is provided. In certain embodiments, the phosphorylated NFAT is attached to a solid support. Calcineurin or a biologically active derivative thereof having enzymatic activity is provided. A candidate agent is provided. An oligonucleotide having an NFAT site is provided. The phosphorylated NFAT, calcineurin or biologically active derivative thereof, and the candidate agent are contacted with each other in reaction media under conditions that allow enzymatic activity of calcineurin. Specific binding of NFAT to the oligonucleotide having the NFAT site is determined. A reduction of binding is indicative of the usefulness of the agent in inhibiting conformational change in NFAT from dephosphorylation by calcineurin. Preferably, the reduction is assessed relative to the same reaction without addition of the candidate agent.

NFAT changes its conformation as a direct consequence of dephosphorylation by calcineurin in such a way as to dramatically increase its specific binding to DNA (Park et al, J. Biol Chem 270:20653-20659 (1995); Shaw et al, Proc Natl Acad Sci USA 92:11205-11209 (1995)). Specific binding of NFAT to DNA can be simply assessed in an assay that is suitable for high throughput screening. Thus, this alteration in DNA binding can be used to detect dephosphorylation of NFAT and to screen for compounds that are capable of inhibiting the dephosphorylation. NFAT in phosphorylated form, obtained as described above, is treated with calcineurin in the presence of a candidate agent to be tested. Preferably, control samples of phosphorylated NFAT are incubated (i) in the absence of calcineurin, (ii) in the presence of calcineurin with no added candidate agent, and (iii) in the presence of calcineurin and known inhibitors, e.g., the 13-mer peptide or 25-mer peptide as described herein, or CsA/cyclophilin complexes. At the end of the incubation, specific binding of NFAT to an oligonucleotide, e.g., a double-stranded oligonucleotide, e.g., DNA, incorporating an NFAT site, e.g., the distal NFAT site of the murine IL-2 promoter (Jain et al, Nature 356:801-804 (1992)) or the P1 site of the murine IL-4 promoter (Rooney et al, Immunity 2:473-483 (1995)), is measured. In one embodiment, this measurement is made by incubating the sample with biotinyl-DNA, incorporating the NFAT binding site, then further incubating with streptavidin-SPA beads and $^{125}$I-labeled antibody against NFAT. In this embodiment, scintillation counting of $^{125}$I label gives a measure of the NFAT-DNA complex that has formed. Compounds of interest in the assay are those that prevent or inhibit the increase in DNA binding that results from incubation of phosphorylated NFAT with calcineurin. In embodiments in which the compounds tested are not separated from NFAT before the DNA binding step, preferably, it is further shown that a compound of interest does not directly inhibit the ability of NFAT to bind to DNA, e.g., by examining DNA binding in the same assay when the test compound is added only after the incubation with calcineurin is completed, or by examining the effect of the compound on the binding of bacterially-expressed NFAT. As is known to one skilled in the art, there are many effectively equivalent methods for measuring the binding of NFAT to DNA including, e.g., recruitment of $^3$H-DNA to NFAT bound via anti-67.1 antiserum (Ho et al, J Biol Chem 269: 28181-28186 (1994)) on protein A-SPA beads, competition by unlabeled NFAT with a fixed amount of 125I-NFAT for binding to biotinyl-DNA immobilized on streptavidin-SPA beads, inclusion in the DNA binding reaction of c-Fos and c-Jun proteins to increase the affinity of the interaction, and using another solid phase support.

In an alternative, the conformational change, and therefore dephosphorylation, may be detected directly by using a probe that recognizes specifically a region or determinant of NFAT that is exposed only after dephosphorylation. An example is the nuclear localization sequence (NLS) of NFAT, which is masked until dephosphorylation, but then becomes accessible for binding of other proteins, e.g., the importin proteins that direct dephosphorylated NFAT to the nucleus in cells. Exposure of the NLS, or of a tag peptide introduced into recombinant NFAT in place of the NLS, may be detected, e.g., in an immunoassay with an appropriate antibody. In another alternative, the conformational change in NFAT may be detected by fluorescence resonance energy transfer (FRET) using a recombinant NFAT protein labeled with appropriate fluorophores at two distinct sites, as has been illustrated for calmodulin (Miyawaki et al, Nature 388:883-887 (1997)), or by FRET between fluorophore-labeled minibodies directed to distinct sites on the surface of NFAT whose relative position changes as a result of the conformational change, or by alteration in the intrinsic fluorescence of NFAT upon dephosphorylation.

The invention also includes a method for high-throughput screening of candidate agents to identify an agent that inhibits calcineurin-dependent import of NFAT into the nucleus of a cell. Cells expressing NFAT are provided. A stimulant that activates NFAT through the calcium/calcineurin pathway is provided. A candidate agent is provided. The cells, stimulant and candidate agent are contacted with each other. The presence or absence of nuclear NFAT in the cells is determined. A reduction in nuclear NFAT is indicative of the agent inhibiting calcineurin-dependent import of NFAT into the nucleus of a cell. Preferably, the reduction is assessed relative to the same reaction without addition of the candidate agent.

This assay is based on the calcineurin-dependent difference in localization of NFAT in unstimulated and stimulated cells. Cells expressing NFAT, e.g., endogenous or recombinant NFAT, are incubated in the presence of a stimulant, e.g., calcium ionophore, a neurotransmitter, or a biologically active peptide, known to trigger activation of NFAT via the calcium/calcineurin pathway (for examples, see Table 1 in Rao et al, Annu. Rev. Immunol. 15:707-747 (1997)). Preferably, control samples of cells are incubated without addition of the stimulant, or in the presence of the stimulant and with known inhibitors of calcineurin-dependent NFAT activation, e.g., CsA and FK506. Determining the presence or absence of nuclear NFAT, and also, preferably cytoplasmic NFAT, can be accomplished by any method known to one skilled in the art. Preferably, localization to the nucleus in samples incubated in the presence of the candidate agent is compared with that of control samples incubated with the stimulant only. Agents are scored as positive if they interfere with the calcineurin-dependent import of NFAT to the cell nucleus.

Examples of determining the localization of NFAT include fixing the cells after the contacting step with histological fixative and examining by microscopy or other means capable of detecting the difference between cells having cytoplasmic NFAT and cells having nuclear NFAT. In some embodiments, NFAT is detected by immunocytochemical staining. In some embodiments, the localization of an NFAT fusion protein, e.g., NFAT-GFP, is detected by fluorescence microscopy. Localization of NFAT to the nucleus can be scored, e.g., by microscopy using visual inspection. In some embodiments, visual inspection is aided by automation, or the localization of NFAT is determined in an automated assay. In certain embodiments of an automated assay, cells are stained with, e.g., two distinct fluorophores, a first fluorophore that detects NFAT (e.g., fluorescently labeled NFAT or fluorescent antibodies that bind to NFAT) and a second fluorophore that labels cell nuclei. In these embodiments, the nuclear localization of NFAT is quantitated by assessing colocalization of the two labels, e.g., the average level of NFAT label is determined in pixels that show nuclear labeling above a designated threshold level that is easily determined by examining the positive and negative control samples. In yet other embodiments, line or raster scanning is used to excite fluorescence, or a method sensitive to the spatial frequency of the fluorescent signal is employed.

As with other assays based on detecting the calcineurin-NFAT interaction or its consequences in cells, assays based on the calcineurin-dependent import of NFAT into the cell nucleus have the advantage that the cell permeability of specific inhibitors identified in the assay is assured.

In some embodiments, these cell-based assays are used to screen, e.g., a retroviral expression library, or other peptide or protein expression libraries, for those recombinant proteins capable of interfering with the calcineurin-mediated activation of NFAT.

The cellular assay examining cytoplasmic or nuclear localization of NFAT is also useful as a diagnostic test to confirm normal physiological function in cells derived from an animal, e.g., human, to detect or classify pathological or abnormal function of immune system cells, or to identify stimuli or sources of activation of immune system cells. For example, an immune disorder can be detected or classified by documenting abnormal activation (constitutively nuclear NFAT protein) in a class of cells, or by documenting an abnormal failure to translocate NFAT in response to a stimulus. In another example, the source of an allergic response can be determined, e.g., by testing candidate allergens for their ability to induce nuclear translocation of NFAT in an indicator mast cell line stably expressing NFAT1(1-460)-GFP, where the indicator mast cells have first been exposed to IgE from an animal or a human, and where further exposure to an effective allergen will therefore cause activation of the cells through their Fc receptors and nuclear import of NFAT-GFP.

The invention includes a method for assessing the state of NFAT activation of immune system cells from an animal. Immune system cells isolated from an animal are provided. The presence or absence of nuclear NFAT in the cells is determined. The presence of nuclear NFAT in the cells is indicative of activation of NFAT in the cells. The cells can be isolated by any method known to those skilled in the art, e.g., by biopsy or aspiration. In certain embodiments, the cells are infiltrating cells at a site of inflammation or in a tumor. Preferably, the presence or absence of nuclear NFAT is determined by histological staining, e.g., immunocytochemical staining, of the cells.

The invention also includes a method for assessing the ability of immune system cells isolated from an animal to respond to an NFAT activating signal. Immune system cells from an animal are provided, the cells being unactivated for NFAT. A stimulant that activates NFAT is provided. The cells are contacted with the stimulant. The presence or absence of nuclear NFAT in the cells is determined. A reduction in nuclear NFAT is indicative of impairment of the ability of the cells to respond to an NFAT activating signal. Preferably, the reduction is assessed relative to cells isolated from a normal animal. This assay can be used, e.g., to monitor the level of immune function in certain immunocompromised patients.

The invention also includes a method for identifying a stimulant that can activate NFAT in immune system cells isolated from an animal. Immune system cells isolated from an animal are provided. A candidate stimulant is provided. The cells are contacted with the candidate stimulant. The presence or absence of nuclear NFAT in the cells is determined. The presence of nuclear NFAT is indicative of the stimulant activating NFAT in the cells. In preferred embodiments, the stimulant is an allergen.

By allergen is meant an agent that elicits IgE-mediated reactions. This assay can be used, e.g., to monitor unresponsiveness to a pathogen or tolerance to a specific antigen.

The invention also includes a method for identifying an allergen. An animal cell line expressing NFAT is provided. IgE from an animal, e.g., a human, is provided. A candidate allergen is provided. The cell line is contacted with the IgE. The cell line is contacted with the candidate allergen. Preferably, the cell line is contacted with the candidate allergen after the cell line is contacted with the IgE. The presence or absence of nuclear NFAT in cells of the cell line is determined. The presence of nuclear NFAT is indicative of the candidate allergen being an allergen.

The following non-limiting examples further illustrate the present invention.

EXAMPLES

Example 1

The SPRIEITPS Sequence of NFAT1 is Involved in Nuclear Import of NFAT1

This example illustrates that mutations in the SPRIEITPS (SEQ ID NO:17) sequence in the conserved motif-2 (CM2) region (amino acid residues 110-118) of the NFAT1 conserved regulatory domain (amino acid residues 100-397) inhibit translocation of the mutant NFAT1 protein from the cytoplasm to the nucleus.

A triple CM2 mutant was generated which disrupts the sequence $^{110}$SPRIEITPS$^{118}$ (SEQ ID NO:17) of NFAT1 by replacing each of the three amino acid residues Arg$^{112}$ (R$^{112}$), Glu$^{14}$ (E$^{114}$), and Thr$^{116}$ (T$^{116}$), with an alanine residue. These mutations were generated following the procedures described in Kunkel et al., Methods Enzymol. 154:367-382 (1987). The mutant proteins were expressed with an HA epitope tag in C1.7W2 murine T cells and in HeLa cells, and analyzed for nuclear translocation in response to ionomycin stimulation. The mutant proteins behaved identically in both cell types. Translocation of wild type and mutant NFAT1 to the nucleus was measured by immunocytochemistry as follows. HeLa cells expressing HA-tagged full length wild type NFAT1 or mutant NFAT1 were left unstimulated or activated with ionomycin (3 µM, 10 min). NFAT1 was detected with mouse anti-HA antibody (12CA5) and Cy3™ goat anti-mouse IgG, and visualized using a rhodamine filter set on a Zeiss Axioskop microscope at a magnification of 630×. Results indicated that the triple CM2 mutation impaired translocation of NFAT1 to the nucleus upon ionomycin stimulation. Wild type NFAT1, as well as the mutant ST21, having two mutations in this same region, in which the two serine residues flanking the SPRIEITPS (SEQ ID NO:17) motif were substituted by alanine residues, showed normal translocation.

The triple CM2 mutations also impaired nuclear translocatior of a GFP fusion protein containing only the N-terminal domain of NFAT1 (amino acids 1-460), NFAT1(1-460)-GFP. 24 h after transfection with a plasmid encoding wild type or mutant NFAT-GFP, the HeLa cells or C1.7W2 murine T cells were left untreated or stimulated with ionomycin (2 µM, 10 min). Nuclear translocation of NFAT1 was visualized by fluorescence microscopy. This impairment of nuclear translocation indicated that the SPRIEITPS (SEQ ID NO:17) motif is involved in the nuclear import of NFAT1, and that the effect of the CM2 mutation does not require an intact DNA binding domain (amino acid residues 398-680 of murine NFAT1) or the C-terminal domain of NFAT1 (amino acid residues 681-923, 681-927 and 681-1064 in the three known isoforms of murine NFAT1).

The role in nuclear translocation of each of the amino acid residues, R$^{112}$, E$^{114}$ and T$^{116}$, was also assessed individually. The single amino acid mutation T$^{116}$ to A, in the SPRIEITPS (SEQ ID NO:17) sequence of NFAT1, inhibited translocation in response to ionomycin stimulation almost to the same extent as did the triple CM2 mutation. Single mutations of R$^{112}$ and E$^{114}$ also impaired translocation, but to a lesser extent than the triple CM2 mutation.

Example 2

The SPRIEITPS Sequence of NFAT1 is Required for Effective Dephosphorylation by Calcineurin This example illustrates that mutations in the SPRIEITPS (SEQ ID NO:17) sequence of NFAT1 inhibit dephosphorylation of the mutant NFAT1 protein by calcineurin.

The inability of the CM2 mutant, containing the three mutations described in Example 1, to translocate to the nucleus correlated with its very limited dephosphorylation in stimulated cells. When transiently expressed either in HeLa cells or in C1.7W2 murine T cells, wild type NFAT1(1-460)-GFP fusion protein was dephosphorylated in response to ionomycin stimulation (3 µM, 10 min) as assessed by its shift in migration on SDS-polyacrylamide gel electrophoresis (SDS-PAGE). The more complete shift observed in C1.7W2 T cells under these conditions reflects the higher level of calcineurin activity in this cell line. In contrast, the triple CM2 mutant NFAT1 (1-460)-GFP showed no change in migration after ionomycin stimulation of HeLa cells, and only a slight shift after stimulation of C1.7W2 T cells, indicating that dephosphorylation was inhibited.

The difference in ionomycin sensitivity between HA-tagged wild type NFAT1(1-460)-GFP and the corresponding triple CM2 mutant was tested in C1.7W2 T cells stimulated with a range of ionomycin concentrations (0.07 to 6 μM) for 10 min. Significant dephosphorylation of HA-tagged wild type NFAT1 was achieved in cells stimulated with 220 nM ionomycin, the dephosphorylation being complete with 660 nM ionomycin. In contrast, dephosphorylation of the CM2 mutant protein was incomplete even in cells stimulated with 6 μM ionomycin, a concentration 10 times higher than that required to induce complete dephosphorylation of wild type NFAT1. Dephosphorylation of both wild type NFAT1 and the CM2 mutant was inhibited by cyclosporin A (CsA)(500 nM), indicating that the dephosphorylation remained calcineurin dependent. Immunocytochemical experiments confirmed that the CM2 mutant did not translocate to the nucleus even in C1.7W2 cells stimulated with 6 μM ionomycin.

The triple CM2 mutant also displayed significantly reduced sensitivity to treatment with exogenous calcineurin in vitro. Cytoplasmic extracts from HeLa cells expressing HA-tagged wild type NFAT1 or the triple CM2 mutant NFAT1 protein were incubated with calcineurin (200 nM-2.5 μM) and calmodulin for 30 min at 30° C. The samples were then resolved by SDS-PAGE and the phosphorylation state was analyzed by Western blotting (Shaw et al., Proc Natl Acad Sci USA 92:11205-11209 (1995); Luo et al., Proc Natl Acad Sci USA 93:8907-8912 (1996)) with anti-HA antibody. Dephosphorylation of wild type NFAT1 was apparent with 200 nM calcineurin, whereas the triple CM2 mutant was markedly less sensitive, with only partial dephosphorylation occurring in the presence of 2.5 μM calcineurin.

The role in NFAT1 dephosphorylation of each of the amino acid residues, $R^{112}$, $E^{114}$ and $T^{116}$, was also assessed individually by Western blotting. The single amino acid substitution $T^{116}$ to A, in the SPRIEITPS (SEQ ID NO:17) sequence of NFAT1, inhibited dephosphorylation in response to ionomycin stimulation almost to the same extent as did the triple CM2 mutation. Single mutations of $R^{112}$ and $E^{114}$ also impaired dephosphorylation, but to a lesser extent than the triple CM2 mutation.

Example 3

Peptides Spanning the SPRIRITPS Sequence of NFAT1 Interfere with Recognition and Dephosphorylation of NFAT1 by Calcineurin This example illustrates that peptides spanning the SPRIEITPS (SEQ ID NO:17) sequence of NFAT1 interfere with recognition and dephosphorylation of NFAT1 by calcineurin.

The results from Examples 1 and 2 indicated that the CM2 mutations in the SPRIEITPS (SEQ ID NO:17) sequence impaired the ability of calcineurin to recognize NFAT1 as a substrate and to dephosphorylate it, either in vivo or in cell extracts. One possibility was that the SPRIEITPS (SEQ ID NO:17) sequence represented a region of NFAT-calcineurin contact and that mutation of this sequence impaired the targeting of calcineurin to NFAT.

To test whether the SPRIEITPS (SEQ ID NO:17) motif was directly involved in the interaction of NFAT with calcineurin, peptides spanning the CM2 motif of wild type and mutant NFAT1 were tested in an NFAT-calcineurin binding assay for their capacity to block calcineurin binding to NFAT1. Two wild type peptides were synthesized which spanned the SPRIEITPS (SEQ ID NO:17) motif, one containing 13 amino acid residues of murine NFAT1 (SEQ ID NO:22) and one containing 25 amino acid residues of NFAT1 (SEQ ID NO:29). In the case of the longer peptide, a tyrosine residue not present in the NFAT1 sequence was appended at the C terminus to facilitate chemical coupling to a carrier protein for production of antisera, and the peptide tested in this and subsequent examples (Examples 4 and 5 infra) was therefore a 26-mer. A corresponding 26-mer peptide incorporating the $R^{112}$ to A, $E^{114}$ to A, and $T^{116}$ to A substitutions of the triple CM2 mutant NFAT1, and with the appended tyrosine residue, was synthesized for use as a control. It is evident from the results below, specifically from the identical effects of the 13-mer peptide and the 26-mer peptide on calcineurin binding and from the lack of effect of the 26-mer mutant peptide on calcineurin binding, that the C-terminal tyrosine residue has no role in inhibiting the protein-protein interaction.

$^{125}$I-labelled calcineurin (14 nM, ~7×10$^5$ cpm) was incubated for 30 min at 4° C. with GST-tagged NFAT1 N-terminal domain (GST NFAT1(1-400)) that had been immobilized on glutathione-Sepharose™ beads (Pharmacia Biotech, Piscataway, N.J.), in the absence or presence of different concentrations (1 μM to 100 μM) of wild type 13-mer peptide, wild type 26-mer peptide, or CM2 mutant 26-mer peptide. At the end of the incubation, the glutathione Sepharose beads with bound NFAT1-calcineurin complexes were washed on 5 μm hydrophilic Durapore PVDF filters (Millipore Corporation, Bedford, Mass.) to remove unbound calcineurin, and NFAT1-bound calcineurin was quantitated using a gamma counter. Both peptides incorporating the wild type sequence SPRIEITPS (SEQ ID NO:17) inhibited the binding of calcineurin to NFAT1. The $IC_{50}$ for inhibition by the wild type peptides was very similar, approximately 15 μM for both the 13-mer and 26-mer. In contrast, the mutated 26-mer peptide incorporating the sequence SPAIAIAPS (SEQ ID NO:82) did not inhibit the NFAT1-calcineurin interaction at concentrations up to 100 μM.

The ability of the SPRIEITPS peptides to inhibit dephosphorylation of NFAT1 by calcineurin in vitro was measured by Western blotting analysis. Cytosolic extracts from HeLa cells stably expressing HA-tagged N-terminal domain NFAT1 (1-460)-GFP were incubated with calcineurin (200 nM) and calmodulin (600 nM) in the presence of different concentrations (16 μM to 2 mM) of wild type 13-mer, wild type 26-mer, and CM2 mutant peptides, during 30 min at 30° C. Controls were done with the calcineurin inhibitors sodium pyrophosphate (10 mM) and cyclosporin A/cyclophilin complexes (15 μM/5 μM). Samples were resolved by SDS-PAGE and dephosphorylation was assessed with anti-HA antibody 12CA5. Both the 13-mer and the 26-mer peptides with wild type sequence SPRIEITPS (SEQ ID NO:17) inhibited dephosphorylation of NFAT1 at concentrations in the range from 16 μM to 400 μM, whereas the 26-mer peptide with sequence SPAIAIAPS (SEQ ID NO:82) was only marginally inhibitory, and only at concentrations above 400 μM. Slightly higher concentrations of the peptides were required to inhibit the in vitro dephosphorylation than were required to inhibit NFAT-calcineurin binding, presumably due to some degradation of the peptides by enzymes present in the cell extracts.

Example 4

The SPRIEITPS Sequence Specifically Targets Calcineurin to NFAT Proteins

This example illustrates that peptides spanning the SPRIEITPS (SEQ ID NO:17) sequence do not interfere generally with calcineurin phosphatase activity.

The 13-mer and 26-mer SPRIEITPS peptides were tested to determine if they acted as general inhibitors of calcineurin phosphatase activity by assaying them on the dephosphorylation of a well characterized calcineurin substrate, the RII phosphopeptide (Blumenthal et al., J. Biol. Chem. 261:8140-8145 (1986)). $^{32}$P-RII phosphopeptide (100 µM; specific activity 1×10$^9$ cpm/µmole) was incubated with calcineurin (100 nM) and calmodulin (600 nM). In some samples, FK506/FKBP12 complexes (10 µM/10 µM), calcineurin autoinhibitory peptide (30 µM to 400 µM), or SPRIEITPS peptide, 13-mer or 26-mer at different concentrations (30 µM to 400 µM) were preincubated with calcineurin before addition of the calcineurin mixture to the RII phosphopeptide samples. The dephosphorylation reaction was allowed to proceed for 30 min at 30° C. after which the reaction was stopped by addition of excess 0.1% trichloroacetic acid, substrate peptide was removed by adsorption onto a cation exchange resin (AG50W; BioRad Laboratories, Hercules, Calif.), and released $^{32}$P label in the supernatant was measured in a liquid scintillation counter. Neither of the SPRIEITPS peptides inhibited dephosphorylation of the RII peptide by calcineurin in the same range of concentrations in which they inhibited NFAT1 dephosphorylation. In the same experiment, calcineurin activity was effectively inhibited by a peptide corresponding to its own autoinhibitory domain and by FK506/FKBP12 complexes.

Moreover, dephosphorylation of the RII regulatory subunit of cAMP-dependent protein kinase, a protein substrate of calcineurin (Blumenthal et al., Biol Chem 261:8140-8145 (1986)) from which the RII phosphopeptide is derived, was not inhibited by a SPRIEITPS peptide from NFAT1 as shown by an in vitro dephosphorylation assay with recombinant RIIα protein. A 6× His tagged RIIα protein (90 nM), $^{32}$P-labelled in vitro by the PKA catalytic subunit, was incubated with calcineurin (200 nM) and calmodulin (600 nM). In some samples, the calcineurin inhibitors sodium pyrophosphate (20 mM), CsA/cyclophilin complexes (15 µM/5 µM), FK506/FKBP12 complexes (4 µM/4 µM), or different concentrations of the 26-mer SPRIEITPS peptide (20 µM to 500 µM) were preincubated with calcineurin during 20 min on ice before adding $^{32}$P-labelled RIIα protein to the mixture. Dephosphorylation was allowed to proceed during 45 min at 30° C., samples were resolved by SDS-PAGE, and the gel was stained with Coomasie Brilliant Blue, dried, and autoradiographed. A phosphorimager was used to quantitate the level of $^{32}$P in each lane. Coomasie Brilliant Blue staining showed that equal amounts of the reaction were loaded in each lane. The dephosphorylation of RIIα was efficiently inhibited by the general phosphatase inhibitor sodium pyrophosphate and by the calcineurin inhibitors CsA/cyclophilin complexes and FK506/FKBP12 complexes. In contrast, the 26-mer SPRIEITPS peptide did not inhibit dephosphorylation when used at the concentrations (20 µM and 100 µM) required to inhibit NFAT1 dephosphorylation, and caused only slight inhibition (18% inhibition) at 500 µM.

Additionally, the 26-mer SPRIEITPS peptide did not inhibit the dephosphorylation of a different protein known to be a calcineurin substrate in vivo, the neuronal cytoskeleton protein Tau (Fleming and Johnson, J. Biochem 209:41-47 (1995); Yamamoto et al., J. Biochem 118:1224-1231 (1995)). Purified GST-Tau immobilized on glutathione-Sepharose beads was phosphorylated by MAP kinase, washed, and incubated with calcineurin (200 nM) and calmodulin (600 nM) during 90 min at 30° C. In some samples, the calcineurin inhibitors sodium pyrophosphate (10 mM) or CsA/cyclophilin complexes (15 µM/5 µM), or wild type 26-mer peptide at different concentrations (20 µM to 500 µM) were preincubated with calcineurin for 20 min on ice before the addition of Tau protein. Samples were resolved by SDS-PAGE and analyzed as above. Dephosphorylation of GST-Tau protein by calcineurin was not inhibited by the SPRIEITPS peptide at concentrations of 20 µM and 100 µM, and was minimally inhibited (10%) at 500 µM, a concentration at which the peptide fully inhibited dephosphorylation of NFAT1. The phosphatase inhibitor sodium pyrophosphate and the calcineurin inhibitor, CsA-cyclophilin complexes, efficiently inhibited dephosphorylation of the GST-Tau protein under these conditions.

In sum, a 13-residue or 26-residue peptide spanning the SPRIEITPS (SEQ ID NO:17) sequence of NFAT1 is a potent inhibitor of the interaction of NFAT1 with calcineurin, while not affecting either the phosphatase activity of the enzyme or its ability to dephosphorylate the other non-NFAT substrates tested.

Example 5

SPRIEITPS Peptides from NFAT1 Also Interfere with Activation of Other NFAT Family Members This example illustrates that peptides spanning the SPRIEITPS (SEQ ID NO:17) sequence from NFAT1 interfere comparably with activation of NFAT2 and NFAT4 despite sequence differences among the NFAT proteins.

The SPRIEITPS (SEQ ID NO:17) sequence of NFAT1 is highly conserved in NFAT2, but only partially conserved in NFAT4 which has a CPSIQITSI (SEQ ID NO:20) sequence. NFAT1, NFAT2 and NFAT4 constitute the group of NFAT members expressed in immune cells. The inhibitory effect of the SPRIEITPS peptides, 13-mer and 26-mer, of NFAT1 on the binding of calcineurin to NFAT1, NFAT2 and NFAT4 was tested. Binding assays of $^{125}$I-calcineurin with GST-tagged N-terminal domains of NFAT1 (residues 1-400), NFAT2 (residues 1-418) and NFAT4 (residues 1-400), in the presence or absence of wild type SPRIEITPS peptides or the mutant control peptide, were done as described above. The results showed that the CM2 peptide inhibited the ability of $^{125}$I-calcineurin to bind to the N-terminal regions of NFAT2 and NFAT4 with a very similar concentration dependence. The IC$_{50}$ for inhibition of NFAT2 and NFAT4 calcineurin binding by the 26-mer peptide was again approximately 15 µM, clearly indicative of a common calcineurin targeting mechanism involving the SPRIEITPS (SEQ ID NO:17) sequence in NFAT1 and the cognate SPRIEITSC (SEQ ID NO:18) and CPSIQITSI (SEQ ID NO:20) sequences in NFAT2 and NFAT4.

Similarly, the 13-mer SPRIEITPS peptide from NFAT1 inhibited dephosphorylation of the N-terminal domain of NFAT4 by calcineurin. The HA-tagged N-terminal domains of NFAT1 and NFAT4 were expressed as the fusion proteins HA-NFAT1(1-460)-GFP and HA-NFAT4(1-407)-GFP in HEK-293 cells. At 24 h after transfection, cytosolic extracts were prepared and equivalent aliquots were incubated without calcineurin or with increasing concentrations of calcineurin/calmodulin complexes (100 nM to 900 nM). Wild type 13-mer peptide of NFAT1 (100 µM or 400 µM final concentration in the dephosphorylation reaction) or mutant 26-mer peptide (400 µM final concentration) was added to the calcineurin/calmodulin preparations 20 min before mixing them with the NFAT-containing cell lysates. Dephosphorylation was allowed to proceed for 30 min at 30° C., and samples were analyzed by SDS-PAGE and Western blotting with anti-HA antibody. Lysates from HEK-293 cells expressing HA-NFAT1(1-460)-GFP or HA-NFAT4(1-407)-GFP incubated with calcineurin showed dephosphorylation of the NFAT proteins at all concentrations of calcineurin tested. The addition of wild type 13-mer SPRIEITPS peptide (100 µM or 400 µM) to the assay inhibited dephosphorylation, with more effective inhibition in the presence of 400 µM peptide, whereas the mutant peptide displayed little or no inhibition even with 400 µM peptide.

Example 6

An NFAT1 SPRIEITPS 19-mer Peptide Displays Immunosuppressive Properties In Vivo

This example illustrates that expression of a fusion protein including an NFAT1 SPRIEITPS 19-mer peptide inhibits NFAT1 activation in vivo as measured by dephosphorylation of NFAT1 in T lymphocytes, nuclear translocation of NFAT1 in T lymphocytes, and NFAT-mediated gene expression in T lymphocytes.

The ability of a GFP-SPRIEITPS-19 fusion protein to inhibit ionomycin-induced dephosphorylation of NFAT1 in T lymphocytes was tested as follows. Ionomycin-induced dephosphorylation of HA-tagged NFAT1(1-460)-GFP in T cells expressing the GFP-SPRIEITPS-19 fusion protein, or expressing related proteins used as controls, was examined by Western blotting analysis. The GFP-SPRIEITPS-19 expression vector was made by introducing a double-stranded oligonucleotide encoding the sequence KPAGASGPSPRIEITPSHEAYD (SEQ ID NO:102) in frame between the BsrGI and NotI sites located 3' to the green fluorescent protein (GFP) coding sequence in the pEGFP-N1 expression vector (CLONTECH, Palo Alto, Calif.). The codons encoding residues AYD at the C-terminal end of the peptide sequence were included for convenience in subcloning, and a stop codon was introduced after the last codon for the peptide sequence. The GFP-SPAIAIAPS-19 construct was made by subcloning a double-stranded oligonucleotide encoding SGPSPAIAIAPSHEAYD (SEQ ID NO:103) between the BspEI and BsiWI sites in the GFP-SPRIEITPS-19 expression plasmid. Constructs expressing unmodified GFP, GFP-wild type peptide fusion protein, or GFP-mutant peptide fusion protein, were cotransfected together with expression vector encoding an HA-tagged N-terminal domain of NFAT1 (NFAT1(1-460)-GFP) into C1.7W2 murine T cells. 24 h post transfection, cells were left untreated or stimulated for 10 min with different concentrations of ionomycin. Whole cell lysates were analyzed for dephosphorylation of NFAT1 by Western blotting with anti-HA antibody and for expression of GFP proteins with anti-GFP antibody. The wild type GFP-SPRIEITPS-19 fusion protein efficiently inhibited ionomycin-induced dephosphorylation of NFAT1, whereas neither GFP alone nor the mutant GFP-SPAIAIAPS-19 protein had any inhibitory effect. Western blotting with anti-GFP antibody showed that the GFP, GFP-SPRIEITPS-19, and GFP-SPAIAIAPS-19 proteins were expressed at comparable levels. The inhibition of NFAT1 dephosphorylation by the wild type GFP-SPRIEITPS 19 protein was incomplete under strong stimulation conditions. This result is in agreement with in vitro assays where the concentration of SPRIEITPS peptide required to inhibit dephosphorylation of NFAT1 and NFAT4 was increasingly higher as the calcineurin concentration in the samples was increased.

The ability of GFP-SPRIEITPS-19 fusion protein to inhibit nuclear translocation of endogenous NFAT1 in T lymphocytes was tested as follows. C1.7W2 murine T cells expressing GFP, GFP-SPRIEITPS-19 (wild type peptide), or GFP-SPAIAIAPS-19 (mutant peptide) were stimulated with ionomycin (2 µM, 10 min) and processed for immunocytochemistry. NFAT1 was visualized with anti-T2B1, a rabbit anti-NFAT1 antiserum directed against the C-terminal peptide of NFAT1 isoform C (Wang et al., Ann. NY Acad. Sci. 766:182-194 (1995)) and Cy3™ labeled donkey anti-rabbit IgG (Jackson ImmunoResearch Laboratories, West Grove, Pa.) using a rhodamine filter set. Simultaneous expression of the GFP constructs in individual cells was assessed by GFP fluorescence using a fluorescein filter set. GFP-SPRIEITPS-19 impaired ionomycin-induced nuclear translocation of NFAT1, whereas the control proteins, GFP and the mutant GFP-SPAIAIAPS-19, did not. Translocation was completely inhibited, however, only in those cells expressing higher levels of the GFP-SPRIEITPS-19 protein, indicating that, under these conditions of strong stimulation, effective inhibition required high intracellular concentration of the peptide.

The ability of GFP-SPRIEITPS-19 fusion protein to inhibit NFAT-driven gene transcription in Jurkat T cells was tested as follows. Jurkat human T cells ($15 \times 10^6$ cells/transfection) were transfected with expression plasmids encoding GFP (9 µg plasmid DNA), wild type GFP-SPRIEITPS-19 fusion protein (variable amounts, supplemented with sufficient plasmid encoding GFP to bring the total plasmid DNA to 9 µg), or mutant GFP-SPAIAIAPS-19 fusion protein, together with an NFAT-driven luciferase reporter plasmid (2 µg). Aliquots of the transfected cells were stimulated 24 h after transfection with PMA (20 nM) and ionomycin (1 µM) for 6 hours and luciferase activity in cell lysates was measured. The results showed that GFP-SPRIEITPS-19 inhibited NFAT-mediated transcription in a concentration-dependent manner, up to greater than 60% inhibition. The mutant GFP-SPAIAIAPS-19 protein was only slightly inhibitory (−10%), and only at high concentrations. Western blotting analysis with anti-GFP antibody confirmed that the GFP proteins were expressed at equivalent levels, and that the amount of protein expressed was proportional to the amount of plasmid DNA transfected. The observation that the GFP-SPRIEITPS-19 fusion protein did not completely inhibit NFAT-driven transcription is consistent with the results described above, which showed that the inhibitory effect of the protein was balanced by the strength of the stimulation conditions, and consistent with the level of intracellular expression of the GFP-fusion protein.

In sum, these results showed that a peptide based on a calcineurin targeting motif of NFAT1 was able to inhibit NFAT1 activation and function in vivo.

Example 7

High-Throughput Screen for Inhibitors of Protein-Protein Interaction Between Calcineurin and NFAT (Using a Washing Step)

This example illustrates a high-throughput screen for inhibitors of protein-protein interaction between calcineurin and NFAT, which utilizes a washing step.

A fusion protein between glutathione S-transferase and NFAT1, GST-NFAT1(1-400) (Luo et al., Proc Natl Acad Sci USA 93:8907-8912 (1996)), is immobilized on glutathione-Sepharose beads (obtained from Pharmacia Biotech, Piscataway, N.J.) by incubation for 30 min at 4° C. in binding buffer (50 mM Tris phosphate pH 8.0, 150 mM NaCl, 5 mM $MgCl_2$, 5 mM 2-mercaptoethanol, 1% Triton X-100, supplemented with 1 mM Na orthovanadate, 20 µM leupeptin, 10 µg/ml aprotinin, 2 mM phenylmethylsulfonyl fluoride). For parallel incubations to monitor nonspecific binding (Luo et al., Proc Natl Acad Sci USA 93:8907-8912 (1996)), equivalent amounts of GST or GST-LSF, where LSF (Shirra et al., Mol Cell Biol 14:5076-5087 (1994)) is a DNA-binding protein unrelated to NFAT, are immobilized on glutathione-Sepharose beads. The beads are washed, resuspended in binding buffer, distributed to multiple wells, and the candidate agents are added. The agents may be supplied as a natural products library, e.g., microbial broths or extracts from diverse stains of bacteria, fungi, and actinomycetes (MDS Panlabs, Bothell, Wash.); a combinatorial chemical library, e.g., an Optiverse™ Screening Library (MDS Panlabs, Bothell, Wash.); an encoded combinatorial chemical library synthesized using ECLiPS™ technology (Pharmacopeia, Princeton, N.J.); or another organical chemical, combinatorial chemical, or natural products library assembled according to methods known to those skilled in the art and formatted for high-throughput screening. Total binding is measured in some samples in the absence of an added candidate agent. As a positive control for inhibition in the assay, binding is assessed in the presence of an effective concentration (200 µM) of a 13-mer or 26-mer peptide of the conserved regulatory domain of NFAT protein described herein which is capable of inhibiting protein-protein interaction between calcineurin and NFAT. The specificity of this positive control inhibition is monitored in incubations with similar concentrations of a mutant peptide described herein which is inactive in inhibiting such interaction. Each reaction is supplemented with 100 µM $CaCl_2$, 800 nM calmodulin (Sigma, St. Louis, Mo.)(to confer calcium responsiveness on calcineurin) and 14 nM $^{125}$I-calcineurin (final concentrations). The incubation is carried out for 30 min at 4° C. Iodinated calcineurin is prepared by the following procedure. Calcineurin (100 µg) in 10 mM Tris phosphate pH 8.0, 120 mM NaCl, 0.1 mM EGTA, 5 mM $MgCl_2$, is iodinated by reaction with 1 mCi carrier-free $Na^{125}I$ (NEN Life Science Products, Boston, Mass.) in the presence of IODO-BEADS™ (Pierce, Rockford, Ill.) for 15 min at 4° C. The radiolabeled protein is separated from free $Na^{125}I$ on a spin column (BioRad Bio-spin 6; Bio-Rad Laboratories, Hercules, Calif.) and stored in aliquots at −80° C. until use.

After incubation, binding reactions are filtered through a 5 µm filter (hydrophilic Durapore PVDF filter; Millipore Corp., Bedford, Mass.) adapted to a multiwell format, to separate bound and unbound $^{125}$I-calcineurin. The filters are rapidly washed under continuous vacuum with 50 mM HEPES pH 7.0, 150 mM NaCl, 5 mM $MgCl_2$, 200 µM $CaCl_2$, 10% glycerol, 1% Triton X-100. The $^{125}$I-calcineurin retained by the immobilized GST fusion proteins is quantified by scintillation counting using a gamma counter. A candidate agent is scored as positive if it reduces the protein-protein interaction of calcineurin and NFAT as assessed by radiolabel bound in the assay.

Those skilled in the art will be aware of many alternative ways to carry out an equivalent assay. For example, the reactions can be suitably modified to use any of the proteins, protein fragments, peptides, or analogues described herein as materials for the assays. The roles of the proteins can be reversed, so that calcineurin is immobilized and NFAT is the radiolabeled compound. The reactions can be carried out with other solid supports or as a solution assay. Those skilled in the art will know that the optimal conditions of incubation and washing may change in such modified assays, and that small adjustments of the conditions may be necessary, including, e.g., changes in the concentrations of proteins, the temperature, salts, pH, or inclusion of additional inhibitors of peptidases and phosphatases in the incubation buffer. Likewise, use of other resins or solid supports may require the inclusion in the incubation of substances to block nonspecific binding to these materials.

Example 8

High-Throughput Screen for Inhibitors of Protein-Protein Interaction Between Calcineurin and NFAT (Without a Washing Step)

This example describes a high-throughput screen for inhibitors of protein-protein interaction between calcineurin and NFAT using a scintillation proximity assay.

Recombinant NFAT1 is immobilized on SPA beads (obtained from Amersham, Arlington Heights, Ill.)—e.g., by binding influenza haemagglutinin-tagged NFAT1 to a mouse monoclonal antibody directed against the haemagglutinin epitope, and thereby to SPA beads derivatized with an anti-mouse antibody (Amersham, Arlington Heights, Ill.); or by binding biotinylated NFAT1 to streptavidin SPA beads (Amersham)—and the beads are washed in the binding buffer described in Example 7 and distributed to replicate wells. Candidate agents are added as described in Example 7, and the reactions for total binding and for inhibition using the 13-mer or 26-mer peptide are constituted as described in Example 7. Each reaction is supplemented with 100 µM $CaCl_2$, 800 nM calmodulin, and 14 nM $^{125}$I-calcineurin (final concentrations), and the incubation is carried out for 30 min at 4° C. Bound radioactivity is quantitated directly in the multiwell plate by scintillation counting. A candidate agent is scored as positive if it reduces the protein-protein interaction of calcineurin and NFAT as assessed by radiolabel bound in the assay.

Example 9

High-Throughput Screen for Inhibitors of Dephosphorylation of NFAT by Calcineurin This example illustrates a high-throughput screen for inhibitors of dephosphorylation of NFAT by calcineurin.

Hexahistidine-tagged human NFAT1(1-415) is purified from bacterial lysates by incubation with $Ni^{2+}$-NTA-agarose in 50 mM Tris pH 8.0, 150 mM NaCl, for 30 min at 4° C. For in vitro labeling with $^{32}$P, NFAT bound on the agarose beads is incubated in 20 mM HEPES pH 7.5, 20 mM $MgCl_2$, 20 µM unlabelled ATP with the addition of 0.17 mCi/ml γ-$^{32}$P-ATP (NEN Life Science Products, Boston, Mass.) and 1700 units/ml of the MAP kinase ERK2 (New England Biolabs, Beverly, Mass.). After 20 min at 30° C., the beads are thoroughly washed to remove the kinase and unincorporated radiolabel, resuspended in phosphatase buffer (50 mM HEPES pH 7.5, 140 mM NaCl, 2 mM $MnCl_2$, 2 mM $CaCl_2$, 15 mM 2-mercaptoethanol), and distributed to multiple wells. Candidate agents, or phosphatase buffer or diluent only, are added to individual reactions. The inhibitory 13-mer peptide or 26-mer peptide described herein is added to individual reactions in a range of final concentrations (100 µM to 2 mM) to serve as positive controls for inhibition. Each reaction is brought to a final volume of 30 µl with the addition of 150 nM calcineurin (Sigma Chemical Co., St. Louis, Mo.) and 500 nM calmodulin (Sigma), and incubated 20 min at 30° C. The supernatant is collected by filtration into a multiwell plate, and released $^{32}$P-phosphate is determined by scintillation counting.

Other formats for the assay involve different methods of separating free phosphate from phosphate covalently bound to protein, utilization of a variety of NFAT substrates, or utilization of NFAT purified from cell extracts. Likewise, radiolabel remaining bound to protein may be measured rather than measuring the radiolabel released. In some embodiments, a chromogenic assay for free phosphate (EnzChek Phosphate Assay Kit; Molecular Probes, Eugene, Oreg.) may be substituted for the radioactive assay, avoiding the use of radioactivity and the need for separation of free phosphate from protein after the incubation with calcineurin.

Other protein kinases are also suitable for preparation of $^{32}$P-labelled NFAT if they incorporate phosphate at sites that are targets for dephosphorylation by calcineurin, and if dephosphorylation of those sites by calcineurin is inhibited by the 13-mer or 26-mer inhibitory peptides described herein as is characteristic of the physiological dephosphorylation by calcineurin. In using other protein kinases, the particular conditions of the labeling reaction will depend on the optimal conditions for enzymatic activity of the kinase used. Likewise, for an optimal assay with different preparations of calcineurin, the concentration of calcineurin or of buffer components such as divalent ions, or reaction time or temperature, may require adjustments that can be determined by routine experimentation.

Example 10

Detection of NFAT Dephosphorylation by Calcineurin Using Antibodies to a Dephosphorylated NFAT Peptide Phosphorylated NFAT1 or HA-tagged phosphorylated NFAT1 in dephosphorylation buffer (80 µl 100 mM HEPES pH 7.4, 100 mM NaCl, 20 mM potassium acetate, 2 mM magnesium acetate, 2 mM dithiothreitol, 0.1 mg/ml bovine serum albumin) is distributed, 0.3 ng/well, to the wells of a multiwell plate. To individual wells is added 20 µl of dephosphorylation buffer alone, of buffer containing a compound to be tested, or of buffer containing 13-mer or 26-mer inhibitory peptide (1-500 µM). Each reaction is brought to a final volume of 120 µl and a final concentration of 1 mM $CaCl_2$, 150 nM calcineurin (Sigma Chemical Co., St. Louis, Mo.) and 500 nM calmodulin (Sigma Chemical Co., St. Louis, Mo.), and incubated 20 min at 30° C. The reaction is stopped by the addition of the calcineurin inhibitors EGTA and sodium pyrophosphate to concentrations of 5 mM and 30 mM, respectively. The contents of each well are transferred to a second multiwell plate coated for an ELISA with anti-dephosphopeptide antibody, and dephosphorylated NFAT is allowed to bind for 3 h at 20° C. The wells are washed three times with phosphate-buffered saline pH 7; incubated with alkaline phosphatase-labeled anti-67.1 antibody (Ho et al., J Biol Chem 269:28181-28186 (1994)) or antiHA tag antibody, as appropriate, 1 h at 20° C.; and again washed three times with phosphate-buffered saline pH 7. Reaction buffer containing the substrate p-nitrophenyl phosphate is added, the alkaline phosphatase reaction is allowed to proceed at 20° C. until color develops in the control samples that were dephosphorylated by calcineurin in the absence of an inhibitor, the reaction is stopped with 3 N NaOH, and absorbance is read at 405 nm. Compounds that inhibit the calcineurin-NFAT interaction are detected by a decreased absorbance, with a threshold decrease for example of 30%.

Example 11

Detection of the Calcineurin-Dependent Change in Intracellular Localization of NFAT1 Using an Antibody Cells expressing NFAT1, e.g. PC12 cells, are plated in L15CO$_2$ medium (Nardone et al., Proc Natl Acad Sci USA 91:4412-4416 (1994)) into replicate wells coated with poly-D-lysine in a 96-well plate. For optimal visualization the cells are allowed to attach to the substrate overnight. Individual wells are preincubated 20 min at 37° C. with medium alone, with medium containing a compound to be tested, or with medium containing known inhibitors of NFAT activation; and then further incubated 20 min at 37° C. with stimulus, e.g. ionomycin 20 µM for PC12 cells, in the continuing presence of test compound or inhibitor in those wells where a test compound or inhibitor is used. The assay is terminated by removal of medium and addition of fixative, 4% paraformaldehyde in 0.12 M phosphate buffer, and fixation is allowed to proceed 30 min at room temperature. The wells are washed 4 times with phosphate-buffered saline, and the fixed cells are permeabilized and preblocked for 30 min at room temperature with phosphate-buffered saline containing 5% fetal calf serum and 0.3% Triton X-100. The primary antibody incubation for immune staining is with anti-67.1 antiserum (Ho et al., J Biol Chem 269:28181-28186 (1994)), followed by washing and incubation with Cy3™-labeled donkey anti-rabbit IgG (Jackson ImmunoResearch Laboratories, West Grove, Pa.). After washing to remove unbound second antibody, the samples are examined by fluorescence microscopy to determine the localization of immune staining for NFAT1, and by phase contrast microscopy to visualize cell nuclei and cytoplasm. With adequate stimulation, as verified by examination of those samples incubated with stimulus alone, not more than ~1% of cells should have cytoplasmic NFAT1. A tested compound is scored positive if a larger fraction of cells displays predominantly cytoplasmic staining for NFAT1, or if significant numbers of cells display some cytoplasmic retention of NFAT1.

Example 12

Detection of the Calcineurin-Dependent Change in Intracellular Localization of NFAT1 Using an NFAT-GFP Fusion Protein HeLa cell line NFAT16, a cell line stably expressing GFP-NFAT1(1-460) under control of the CMV promoter, is plated in a 96-well plate suitable for subsequent fluorescence microscopy, and incubated overnight in Dulbecco's modified Eagle medium supplemented with 10% fetal calf serum, 10 mM HEPES, 2 mM L-glutamine, and 1 mg/ml neomycin to permit spreading of cells on the substrate for optimal visualization. A preincubation is initiated by withdrawal of the growth medium, and addition of the same medium containing (in individual wells) either a compound to be tested, a known inhibitor of NFAT activation and nuclear translocation (e.g., CsA), or no additive. After a 30 min preincubation, the incubation is supplemented with an additional 3 mM $CaCl_2$ and with ionomycin to 3 µM final concentration, except that no ionomycin is added to the designated unstimulated control wells. The purpose of the additional $Ca^{2+}$ is to ensure optimal activation of NFAT in this cell line. The incubation is continued at 37° C. for 10 min. The medium is aspirated, and the cells are fixed by treatment with 3% paraformaldehyde in 0.1 M sodium phosphate, pH 7.4, for 30 min at room temperature. Fixative is removed by washing three times, 5 min each, with phosphate-buffered saline. Localization of NFAT1(1-460)-GFP in the cells is examined by fluorescence microscopy using suitable excitation and emission filters for GFP, and nuclei and cytoplasm are visualized by phase contrast microscopy. Less than 5% of stimulated NFAT16 cells show predominantly cytoplasmic NFAT-GFP fluorescence under the stated conditions. A tested compound is scored positive if a larger fraction of cells, for example more than 10% of cells, displays predominantly cytoplasmic staining for NFAT1.

Many available cell lines, primary cells, or cells expressing recombinant NFAT display a calcineurin-dependent translocation of NFAT to the cell nucleus. Those skilled in the art will know that for adequate stimulation of different cell types, adjustments are made in the conditions of the assay, e.g., in the stimulus used, the concentration of stimulus, the time of incubation with stimulus, and the addition of $CaCl_2$. In each case, appropriate assay conditions for the cells studied can be determined by routine experimentation.

Those skilled in the art will be able to ascertain using no more than routine experimentation, many equivalents of the specific embodiments of the invention described herein. These and all other equivalents are intended to be encompassed by the following claims.

What is claimed is:

1. An NFAT derivative comprising the sequence of SEQ ID NO:22, wherein at least one non-conserved residue in SEQ ID NO:22 is substituted, and wherein the NFAT derivative is less than 50 amino acid residues long and binds to calcineurin.

2. The NFAT derivative of claim 1, wherein the NFAT derivative is less than 20 amino acid residues long.

3. A peptide inhibitor of protein-protein interaction between calcineurin and NFAT identified by a process comprising the steps of:
   providing a first compound comprising NFAT or a biologically active derivative thereof;
   providing a second compound comprising calcineurin or a biologically active derivative thereof;
   providing a candidate agent;
   contacting said first compound, said second compound and said candidate agent with each other;
   determining the amount of said second compound bound to said first compound or determining the amount of said first compound bound to said second compound, wherein a reduction in binding between said first compound and said second compound indicates that said candidate agent is an inhibitor of protein-protein interaction between calcineurin and NFAT; and
   wherein the peptide inhibitor is an NFAT derivative comprising the sequence of SEQ ID NO:22, wherein at least one non-conserved residue in SEQ ID NO:22 is substituted, and wherein the NFAT derivative is less than 150 amino acid residues long and binds to calcineurin.

4. The peptide inhibitor of claim 3, wherein the NFAT derivative is less than 20 amino acid residues long.

5. An NFAT derivative comprising the sequence of SEQ ID NO:5, wherein at least one non-conserved residue in SEQ ID NO:5 is substituted, and wherein the NFAT derivative is less than 50 amino acid residues long and binds to calcineurin.

6. The NFAT derivative of claim 5, wherein the NFAT derivative is less than 20 amino acid residues long.

7. The NFAT derivative of claim 5, wherein the NFAT derivative is less than 10 amino acid residues long.

8. The NFAT derivative of claim 5, wherein the NFAT derivative is 6 amino acid residues long.

9. A peptide inhibitor of protein-protein interaction between calcineurin and NFAT identified by a process comprising the steps of:
   providing a first compound comprising NFAT or a biologically active derivative thereof;
   providing a second compound comprising calcineurin or a biologically active derivative thereof;
   providing a candidate agent;
   contacting said first compound, said second compound and said candidate agent with each other;
   determining the amount of said second compound bound to said first compound or determining the amount of said first compound bound to said second compound, wherein a reduction in binding between said first compound and said second compound indicates that said candidate agent is an inhibitor of protein-protein interaction between calcineurin and NFAT; and
   wherein the peptide inhibitor is an NFAT derivative comprising the sequence of SEQ ID NO:5, wherein at least one non-conserved residue in SEQ ID NO:5 is substituted, and wherein the NFAT derivative is less than 150 amino acid residues long and binds to calcineurin.

10. The peptide inhibitor of claim 9, wherein the NFAT derivative is less than 20 amino acid residues long.

11. The peptide inhibitor of claim 9, wherein the peptide inhibitor is less than 10 amino acid residues long.

12. The peptide inhibitor of claim 9, wherein the peptide inhibitor is 6 amino acid residues long.

13. The NFAT derivative of claim 1, wherein the NFAT derivative is 13 amino acid residues long.

14. The peptide inhibitor of claim 3, wherein the peptide inhibitor is less than 100 amino acid residues long.

15. The peptide inhibitor of claim 3, wherein the peptide inhibitor is less than 50 amino acid residues long.

16. The peptide inhibitor of claim 3, wherein the peptide inhibitor is 13 amino acid residues long.

17. The peptide inhibitor of claim 9, wherein the NFAT derivative is less than 100 amino acid residues long.

18. The peptide inhibitor of claim 9, wherein the NFAT derivative is less than 50 amino acid residues long.

* * * * *

SEQUENCE LISTING

```
<160> NUMBER OF SEQ ID NOS: 114

<210> SEQ ID NO 1
<211> LENGTH: 5
<212> TYPE: PRT
<213> ORGANISM: Homo sapiens

<400> SEQUENCE: 1

Arg Ile Glu Ile Thr
1               5

<210> SEQ ID NO 2
<211> LENGTH: 5
<212> TYPE: PRT
<213> ORGANISM: Homo sapiens

<400> SEQUENCE: 2

Ser Ile Arg Ile Thr
1               5

<210> SEQ ID NO 3
<211> LENGTH: 5
<212> TYPE: PRT
<213> ORGANISM: Homo sapiens

<400> SEQUENCE: 3

Ser Ile Gln Ile Thr
1               5

<210> SEQ ID NO 4
<211> LENGTH: 5
<212> TYPE: PRT
<213> ORGANISM: Mus musculus

<400> SEQUENCE: 4

Ser Ile Gln Phe Thr
1               5

<210> SEQ ID NO 5
<211> LENGTH: 6
<212> TYPE: PRT
<213> ORGANISM: Homo sapiens

<400> SEQUENCE: 5

Pro Arg Ile Glu Ile Thr
1               5
```

```
<210> SEQ ID NO 6
<211> LENGTH: 6
<212> TYPE: PRT
<213> ORGANISM: Homo sapiens

<400> SEQUENCE: 6

Pro Ser Ile Arg Ile Thr
1               5

<210> SEQ ID NO 7
<211> LENGTH: 6
<212> TYPE: PRT
<213> ORGANISM: Mus musculus

<400> SEQUENCE: 7

Pro Ser Ile Gln Phe Thr
1               5

<210> SEQ ID NO 8
<211> LENGTH: 7
<212> TYPE: PRT
<213> ORGANISM: Homo sapiens

<400> SEQUENCE: 8

Ser Pro Arg Ile Glu Ile Thr
1               5

<210> SEQ ID NO 9
<211> LENGTH: 7
<212> TYPE: PRT
<213> ORGANISM: Homo sapiens

<400> SEQUENCE: 9

Cys Pro Ser Ile Arg Ile Thr
1               5

<210> SEQ ID NO 10
<211> LENGTH: 7
<212> TYPE: PRT
<213> ORGANISM: Homo sapiens

<400> SEQUENCE: 10

Cys Pro Ser Ile Gln Ile Thr
1               5

<210> SEQ ID NO 11
<211> LENGTH: 7
<212> TYPE: PRT
<213> ORGANISM: Mus musculus

<400> SEQUENCE: 11

Cys Pro Ser Ile Gln Phe Thr
1               5

<210> SEQ ID NO 12
<211> LENGTH: 8
<212> TYPE: PRT
<213> ORGANISM: Homo sapiens

<400> SEQUENCE: 12

Ser Pro Arg Ile Glu Ile Thr Pro
1               5

<210> SEQ ID NO 13
<211> LENGTH: 8
```

```
<212> TYPE: PRT
<213> ORGANISM: Homo sapiens

<400> SEQUENCE: 13

Ser Pro Arg Ile Glu Ile Thr Ser
1               5

<210> SEQ ID NO 14
<211> LENGTH: 8
<212> TYPE: PRT
<213> ORGANISM: Homo sapiens

<400> SEQUENCE: 14

Cys Pro Ser Ile Arg Ile Thr Ser
1               5

<210> SEQ ID NO 15
<211> LENGTH: 8
<212> TYPE: PRT
<213> ORGANISM: Homo sapiens

<400> SEQUENCE: 15

Cys Pro Ser Ile Gln Ile Thr Ser
1               5

<210> SEQ ID NO 16
<211> LENGTH: 8
<212> TYPE: PRT
<213> ORGANISM: Mus musculus

<400> SEQUENCE: 16

Cys Pro Ser Ile Gln Phe Thr Ser
1               5

<210> SEQ ID NO 17
<211> LENGTH: 9
<212> TYPE: PRT
<213> ORGANISM: Homo sapiens

<400> SEQUENCE: 17

Ser Pro Arg Ile Glu Ile Thr Pro Ser
1               5

<210> SEQ ID NO 18
<211> LENGTH: 9
<212> TYPE: PRT
<213> ORGANISM: Homo sapiens

<400> SEQUENCE: 18

Ser Pro Arg Ile Glu Ile Thr Ser Cys
1               5

<210> SEQ ID NO 19
<211> LENGTH: 9
<212> TYPE: PRT
<213> ORGANISM: Homo sapiens

<400> SEQUENCE: 19

Cys Pro Ser Ile Arg Ile Thr Ser Ile
1               5

<210> SEQ ID NO 20
<211> LENGTH: 9
<212> TYPE: PRT
<213> ORGANISM: Homo sapiens
```

```
<400> SEQUENCE: 20

Cys Pro Ser Ile Gln Ile Thr Ser Ile
1               5

<210> SEQ ID NO 21
<211> LENGTH: 9
<212> TYPE: PRT
<213> ORGANISM: Mus musculus

<400> SEQUENCE: 21

Cys Pro Ser Ile Gln Phe Thr Ser Ile
1               5

<210> SEQ ID NO 22
<211> LENGTH: 13
<212> TYPE: PRT
<213> ORGANISM: Mus musculus

<400> SEQUENCE: 22

Ser Gly Pro Ser Pro Arg Ile Glu Ile Thr Pro Ser His
1               5                   10

<210> SEQ ID NO 23
<211> LENGTH: 13
<212> TYPE: PRT
<213> ORGANISM: Homo sapiens

<400> SEQUENCE: 23

Ser Gly Leu Ser Pro Arg Ile Glu Ile Thr Pro Ser His
1               5                   10

<210> SEQ ID NO 24
<211> LENGTH: 13
<212> TYPE: PRT
<213> ORGANISM: Homo sapiens

<400> SEQUENCE: 24

Ala Leu Glu Ser Pro Arg Ile Glu Ile Thr Ser Cys Leu
1               5                   10

<210> SEQ ID NO 25
<211> LENGTH: 13
<212> TYPE: PRT
<213> ORGANISM: Homo sapiens

<400> SEQUENCE: 25

Val Leu Glu Cys Pro Ser Ile Arg Ile Thr Ser Ile Ser
1               5                   10

<210> SEQ ID NO 26
<211> LENGTH: 13
<212> TYPE: PRT
<213> ORGANISM: Homo sapiens

<400> SEQUENCE: 26

Pro Phe Glu Cys Pro Ser Ile Gln Ile Thr Ser Ile Ser
1               5                   10

<210> SEQ ID NO 27
<211> LENGTH: 13
<212> TYPE: PRT
<213> ORGANISM: Mus musculus

<400> SEQUENCE: 27
```

```
Pro Phe Glu Cys Pro Ser Ile Gln Ile Thr Ser Ile Ser
  1               5                  10
```

<210> SEQ ID NO 28
<211> LENGTH: 13
<212> TYPE: PRT
<213> ORGANISM: Mus musculus

<400> SEQUENCE: 28

```
Pro Phe Glu Cys Pro Ser Ile Gln Phe Thr Ser Ile Ser
  1               5                  10
```

<210> SEQ ID NO 29
<211> LENGTH: 25
<212> TYPE: PRT
<213> ORGANISM: Mus musculus

<400> SEQUENCE: 29

```
Lys Pro Ala Gly Ala Ser Gly Pro Ser Pro Arg Ile Glu Ile Thr Pro
  1               5                  10                  15

Ser His Glu Leu Met Gln Ala Gly Gly
              20                  25
```

<210> SEQ ID NO 30
<211> LENGTH: 25
<212> TYPE: PRT
<213> ORGANISM: Homo sapiens

<400> SEQUENCE: 30

```
Lys Pro Ala Gly Ala Ser Gly Leu Ser Pro Arg Ile Glu Ile Thr Pro
  1               5                  10                  15

Ser His Glu Leu Ile Gln Ala Val Gly
              20                  25
```

<210> SEQ ID NO 31
<211> LENGTH: 25
<212> TYPE: PRT
<213> ORGANISM: Homo sapiens

<400> SEQUENCE: 31

```
Pro Asp Gly Ala Pro Ala Leu Glu Ser Pro Arg Ile Glu Ile Thr Ser
  1               5                  10                  15

Cys Leu Gly Leu Tyr His Asn Asn Asn
              20                  25
```

<210> SEQ ID NO 32
<211> LENGTH: 25
<212> TYPE: PRT
<213> ORGANISM: Homo sapiens

<400> SEQUENCE: 32

```
Ala Gly Gly Gly Arg Val Leu Glu Cys Pro Ser Ile Arg Ile Thr Ser
  1               5                  10                  15

Ile Ser Pro Thr Pro Glu Pro Pro Ala
              20                  25
```

<210> SEQ ID NO 33
<211> LENGTH: 25
<212> TYPE: PRT
<213> ORGANISM: Homo sapiens

<400> SEQUENCE: 33

-continued

Leu Gly Gly Pro Lys Pro Phe Glu Cys Pro Ser Ile Gln Ile Thr Ser
1               5                   10                  15

Ile Ser Pro Asn Cys His Gln Glu Leu
            20              25

<210> SEQ ID NO 34
<211> LENGTH: 25
<212> TYPE: PRT
<213> ORGANISM: Mus musculus

<400> SEQUENCE: 34

Leu Gly Gly Pro Lys Pro Phe Glu Cys Pro Ser Ile Gln Ile Thr Ser
1               5                   10                  15

Ile Ser Pro Asn Cys His Gln Gly Thr
            20              25

<210> SEQ ID NO 35
<211> LENGTH: 25
<212> TYPE: PRT
<213> ORGANISM: Mus musculus

<400> SEQUENCE: 35

Leu Gly Gly Pro Lys Pro Phe Glu Cys Pro Ser Ile Gln Phe Thr Ser
1               5                   10                  15

Ile Ser Pro Asn Cys Gln Gln Glu Leu
            20              25

<210> SEQ ID NO 36
<211> LENGTH: 15
<212> TYPE: DNA
<213> ORGANISM: Homo sapiens

<400> SEQUENCE: 36
cggatcgaga tcact                                                  15

<210> SEQ ID NO 37
<211> LENGTH: 15
<212> TYPE: DNA
<213> ORGANISM: Homo sapiens

<400> SEQUENCE: 37
agcatccgca tcacc                                                  15

<210> SEQ ID NO 38
<211> LENGTH: 15
<212> TYPE: DNA
<213> ORGANISM: Homo sapiens

<400> SEQUENCE: 38
agtattcaaa ttaca                                                  15

<210> SEQ ID NO 39
<211> LENGTH: 15
<212> TYPE: DNA
<213> ORGANISM: Mus musculus

<400> SEQUENCE: 39
agtatccaat ttaca                                                  15

<210> SEQ ID NO 40
<211> LENGTH: 18
<212> TYPE: DNA
<213> ORGANISM: Homo sapiens

```
<400> SEQUENCE: 40
cctcggatcg agatcact                                              18

<210> SEQ ID NO 41
<211> LENGTH: 18
<212> TYPE: DNA
<213> ORGANISM: Homo sapiens

<400> SEQUENCE: 41
cccagcatcc gcatcacc                                              18

<210> SEQ ID NO 42
<211> LENGTH: 18
<212> TYPE: DNA
<213> ORGANISM: Mus musculus

<400> SEQUENCE: 42
ccaagtatcc aatttaca                                              18

<210> SEQ ID NO 43
<211> LENGTH: 21
<212> TYPE: DNA
<213> ORGANISM: Homo sapiens

<400> SEQUENCE: 43
agccctcgga tcgagatcac t                                          21

<210> SEQ ID NO 44
<211> LENGTH: 21
<212> TYPE: DNA
<213> ORGANISM: Homo sapiens

<400> SEQUENCE: 44
tgtcccagca tccgcatcac c                                          21

<210> SEQ ID NO 45
<211> LENGTH: 21
<212> TYPE: DNA
<213> ORGANISM: Homo sapiens

<400> SEQUENCE: 45
tgcccaagta ttcaaattac a                                          21

<210> SEQ ID NO 46
<211> LENGTH: 21
<212> TYPE: DNA
<213> ORGANISM: Mus musculus

<400> SEQUENCE: 46
tgcccaagta tccaatttac a                                          21

<210> SEQ ID NO 47
<211> LENGTH: 24
<212> TYPE: DNA
<213> ORGANISM: Homo sapiens

<400> SEQUENCE: 47
agccctcgga tcgagatcac tcca                                       24

<210> SEQ ID NO 48
<211> LENGTH: 24
<212> TYPE: DNA
```

<213> ORGANISM: Homo sapiens

<400> SEQUENCE: 48
agtcctcgca tcgagataac ctcg                                    24

<210> SEQ ID NO 49
<211> LENGTH: 24
<212> TYPE: DNA
<213> ORGANISM: Homo sapiens

<400> SEQUENCE: 49
tgtcccagca tccgcatcac ctcc                                    24

<210> SEQ ID NO 50
<211> LENGTH: 24
<212> TYPE: DNA
<213> ORGANISM: Homo sapiens

<400> SEQUENCE: 50
tgcccaagta ttcaaattac atct                                    24

<210> SEQ ID NO 51
<211> LENGTH: 24
<212> TYPE: DNA
<213> ORGANISM: Mus musculus

<400> SEQUENCE: 51
tgcccaagta tccaatttac atct                                    24

<210> SEQ ID NO 52
<211> LENGTH: 27
<212> TYPE: DNA
<213> ORGANISM: Homo sapiens

<400> SEQUENCE: 52
agccctcgga tcgagatcac tccatcc                                 27

<210> SEQ ID NO 53
<211> LENGTH: 27
<212> TYPE: DNA
<213> ORGANISM: Homo sapiens

<400> SEQUENCE: 53
agtcctcgca tcgagataac ctcgtgc                                 27

<210> SEQ ID NO 54
<211> LENGTH: 27
<212> TYPE: DNA
<213> ORGANISM: Homo sapiens

<400> SEQUENCE: 54
tgtcccagca tccgcatcac ctccatc                                 27

<210> SEQ ID NO 55
<211> LENGTH: 27
<212> TYPE: DNA
<213> ORGANISM: Homo sapiens

<400> SEQUENCE: 55
tgcccaagta ttcaaattac atctatc                                 27

<210> SEQ ID NO 56
<211> LENGTH: 27

```
<212> TYPE: DNA
<213> ORGANISM: Mus musculus

<400> SEQUENCE: 56
tgcccaagta tccaatttac atctatc                                              27

<210> SEQ ID NO 57
<211> LENGTH: 39
<212> TYPE: DNA
<213> ORGANISM: Mus musculus

<400> SEQUENCE: 57
tcgggcccga gccctcggat cgagatcact ccatcccac                                  39

<210> SEQ ID NO 58
<211> LENGTH: 39
<212> TYPE: DNA
<213> ORGANISM: Homo sapiens

<400> SEQUENCE: 58
tcgggcctga gccctcggat cgagatcact ccgtcccac                                  39

<210> SEQ ID NO 59
<211> LENGTH: 39
<212> TYPE: DNA
<213> ORGANISM: Homo sapiens

<400> SEQUENCE: 59
gccctggaga gtcctcgcat cgagataacc tcgtgcttg                                  39

<210> SEQ ID NO 60
<211> LENGTH: 39
<212> TYPE: DNA
<213> ORGANISM: Homo sapiens

<400> SEQUENCE: 60
gttctcgagt gtcccagcat ccgcatcacc tccatctct                                  39

<210> SEQ ID NO 61
<211> LENGTH: 39
<212> TYPE: DNA
<213> ORGANISM: Homo sapiens

<400> SEQUENCE: 61
ccctttgagt gcccaagtat tcaaattaca tctatctct                                  39

<210> SEQ ID NO 62
<211> LENGTH: 39
<212> TYPE: DNA
<213> ORGANISM: Mus musculus

<400> SEQUENCE: 62 cccttttgagt gcccaagtat tcaaatcaca tccatttct                                 39

<210> SEQ ID NO 63
<211> LENGTH: 39
<212> TYPE: DNA
<213> ORGANISM: Mus musculus

<400> SEQUENCE: 63 cccttttgagt gcccaagtat ccaatttaca tctatctct                                 39

<210> SEQ ID NO 64
```

```
<211> LENGTH: 75
<212> TYPE: DNA
<213> ORGANISM: Mus musculus

<400> SEQUENCE: 64
aagccagcag gggcttcggg cccgagccct cggatcgaga tcactccatc ccacgaactg    60
atgcaggcag ggggg                                                     75

<210> SEQ ID NO 65
<211> LENGTH: 75
<212> TYPE: DNA
<213> ORGANISM: Homo sapiens

<400> SEQUENCE: 65
aagccagcag gggcctcggg cctgagccct cggatcgaga tcactccgtc ccacgaactg    60
atccaggcag tgggg                                                     75

<210> SEQ ID NO 66
<211> LENGTH: 75
<212> TYPE: DNA
<213> ORGANISM: Homo sapiens

<400> SEQUENCE: 66
cctgatgggg cccctgccct ggagagtcct cgcatcgaga taacctcgtg cttgggcctg    60
taccacaaca ataac                                                     75

<210> SEQ ID NO 67
<211> LENGTH: 75
<212> TYPE: DNA
<213> ORGANISM: Homo sapiens

<400> SEQUENCE: 67 gctggggtg gccgtgttct cgagtgtccc agcatccgca tcacctccat ctctcccacg     60
ccggagccgc cagca                                                     75

<210> SEQ ID NO 68
<211> LENGTH: 75
<212> TYPE: DNA
<213> ORGANISM: Homo sapiens

<400> SEQUENCE: 68
ttaggtggtc ccaaacccttt tgagtgccca agtattcaaa ttacatctat ctctcctaac   60
tgtcatcaag aatta                                                     75

<210> SEQ ID NO 69
<211> LENGTH: 75
<212> TYPE: DNA
<213> ORGANISM: Mus musculus

<400> SEQUENCE: 69
ttaggtggtc ctaaaccctt tgagtgccca agtattcaaa tcacatccat ttctcctaac    60
tgtcatcaag gaaca                                                     75

<210> SEQ ID NO 70
<211> LENGTH: 75
<212> TYPE: DNA
<213> ORGANISM: Mus musculus

<400> SEQUENCE: 70
ttaggtggtc ccaaaccctt tgagtgccca agtatccaat ttacatctat ctctcctaac    60
```

```
tgtcaacaag aatta                                                    75
```

<210> SEQ ID NO 71
<211> LENGTH: 6
<212> TYPE: PRT
<213> ORGANISM: Homo sapiens

<400> SEQUENCE: 71

Pro Ser Ile Gln Ile Thr
 1               5

<210> SEQ ID NO 72
<211> LENGTH: 18
<212> TYPE: DNA
<213> ORGANISM: Homo sapiens

<400> SEQUENCE: 72

```
ccaagtattc aaattaca                                                 18
```

<210> SEQ ID NO 73
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Arg, or Ser
<220> FEATURE:
<221> NAME/KEY: VARIANT
<222> LOCATION: 3
<223> OTHER INFORMATION: Xaa = Glu, Arg, or Gln
<220> FEATURE:
<221> NAME/KEY: VARIANT
<222> LOCATION: 4
<223> OTHER INFORMATION: Xaa = Ile, or Phe

<400> SEQUENCE: 73

Xaa Ile Xaa Xaa Thr
 1               5

<210> SEQ ID NO 74
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Arg, or Ser
<220> FEATURE:
<221> NAME/KEY: VARIANT
<222> LOCATION: 3
<223> OTHER INFORMATION: Xaa = Glu, Arg, or Gln

<400> SEQUENCE: 74

Xaa Ile Xaa Ile Thr
 1               5

<210> SEQ ID NO 75
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT

```
<222> LOCATION: 3
<223> OTHER INFORMATION: Xaa = Glu, Arg, or Gln

<400> SEQUENCE: 75

Arg Ile Xaa Ile Thr
 1               5

<210> SEQ ID NO 76
<211> LENGTH: 5
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Arg, or Ser

<400> SEQUENCE: 76

Xaa Ile Glu Ile Thr
 1               5

<210> SEQ ID NO 77
<211> LENGTH: 6
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 2
<223> OTHER INFORMATION: Xaa = Arg, or Ser
<220> FEATURE:
<221> NAME/KEY: VARIANT
<222> LOCATION: 4
<223> OTHER INFORMATION: Xaa = Glu, Arg, or Gln
<220> FEATURE:
<221> NAME/KEY: VARIANT
<222> LOCATION: 5
<223> OTHER INFORMATION: Xaa = Ile, or Phe

<400> SEQUENCE: 77

Pro Xaa Ile Xaa Xaa Thr
 1               5

<210> SEQ ID NO 78
<211> LENGTH: 7
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Ser, or Cys
<220> FEATURE:
<221> NAME/KEY: VARIANT
<222> LOCATION: 3
<223> OTHER INFORMATION: Xaa = Arg, or Ser
<220> FEATURE:
<221> NAME/KEY: VARIANT
<222> LOCATION: 5
<223> OTHER INFORMATION: Xaa = Glu, Arg, or Gln
<220> FEATURE:
<221> NAME/KEY: VARIANT
<222> LOCATION: 6
<223> OTHER INFORMATION: Xaa = Ile, or Phe

<400> SEQUENCE: 78

Xaa Pro Xaa Ile Xaa Xaa Thr
 1               5
```

```
<210> SEQ ID NO 79
<211> LENGTH: 8
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Ser, or Cys
<220> FEATURE:
<221> NAME/KEY: VARIANT
<222> LOCATION: 3
<223> OTHER INFORMATION: Xaa = Arg, or Ser
<220> FEATURE:
<221> NAME/KEY: VARIANT
<222> LOCATION: 5
<223> OTHER INFORMATION: Xaa = Glu, Arg, or Gln
<220> FEATURE:
<221> NAME/KEY: VARIANT
<222> LOCATION: 6
<223> OTHER INFORMATION: Xaa = Ile, or Phe
<220> FEATURE:
<221> NAME/KEY: VARIANT
<222> LOCATION: 8
<223> OTHER INFORMATION: Xaa = Pro, or Ser

<400> SEQUENCE: 79

Xaa Pro Xaa Ile Xaa Xaa Thr Xaa
 1               5

<210> SEQ ID NO 80
<211> LENGTH: 9
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1
<223> OTHER INFORMATION: Xaa = Ser, or Cys
<220> FEATURE:
<221> NAME/KEY: VARIANT
<222> LOCATION: 3
<223> OTHER INFORMATION: Xaa = Arg, or Ser
<220> FEATURE:
<221> NAME/KEY: VARIANT
<222> LOCATION: 5
<223> OTHER INFORMATION: Xaa = Glu, Arg, or Gln
<220> FEATURE:
<221> NAME/KEY: VARIANT
<222> LOCATION: 6
<223> OTHER INFORMATION: Xaa = Ile, or Phe
<220> FEATURE:
<221> NAME/KEY: VARIANT
<222> LOCATION: 8
<223> OTHER INFORMATION: Xaa = Pro, or Ser
<220> FEATURE:
<221> NAME/KEY: VARIANT
<222> LOCATION: 9
<223> OTHER INFORMATION: Xaa = Ser, Cys, or Ile

<400> SEQUENCE: 80

Xaa Pro Xaa Ile Xaa Xaa Thr Xaa Xaa
 1               5

<210> SEQ ID NO 81
<211> LENGTH: 13
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
```

```
<222> LOCATION: 1
<223> OTHER INFORMATION: Xaa = Ser, Ala, Val, or Pro
<220> FEATURE:
<221> NAME/KEY: VARIANT
<222> LOCATION: 2
<223> OTHER INFORMATION: Xaa = Gly, Leu, or Phe
<220> FEATURE:
<221> NAME/KEY: VARIANT
<222> LOCATION: 3
<223> OTHER INFORMATION: Xaa = Pro, Leu, or Glu
<220> FEATURE:
<221> NAME/KEY: VARIANT
<222> LOCATION: 4
<223> OTHER INFORMATION: Xaa = Ser, or Cys
<220> FEATURE:
<221> NAME/KEY: VARIANT
<222> LOCATION: 6
<223> OTHER INFORMATION: Xaa = Arg, or Ser
<220> FEATURE:
<221> NAME/KEY: VARIANT
<222> LOCATION: 8
<223> OTHER INFORMATION: Xaa = Glu, Arg, or Gln
<220> FEATURE:
<221> NAME/KEY: VARIANT
<222> LOCATION: 9
<223> OTHER INFORMATION: Xaa = Ile, or Phe
<220> FEATURE:
<221> NAME/KEY: VARIANT
<222> LOCATION: 11
<223> OTHER INFORMATION: Xaa = Pro, or Ser
<220> FEATURE:
<221> NAME/KEY: VARIANT
<222> LOCATION: 12
<223> OTHER INFORMATION: Xaa = Ser, Cys, or Ile
<220> FEATURE:
<221> NAME/KEY: VARIANT
<222> LOCATION: 13
<223> OTHER INFORMATION: Xaa = His, Leu, or Ser

<400> SEQUENCE: 81

Xaa Xaa Xaa Xaa Pro Xaa Ile Xaa Xaa Thr Xaa Xaa Xaa
 1               5                   10

<210> SEQ ID NO 82
<211> LENGTH: 9
<212> TYPE: PRT
<213> ORGANISM: Artificial Sequence
<220> FEATURE:
<223> OTHER INFORMATION: mutated wild type amino acid sequence
      SPRIEITPS

<400> SEQUENCE: 82

Ser Pro Ala Ile Ala Ile Ala Pro Ser
 1               5

<210> SEQ ID NO 83
<211> LENGTH: 15
<212> TYPE: DNA
<213> ORGANISM: Homo sapiens

<400> SEQUENCE: 83
cgcatcgaga taacc                                                      15

<210> SEQ ID NO 84
<211> LENGTH: 15
<212> TYPE: DNA
<213> ORGANISM: Homo sapiens

<400> SEQUENCE: 84
agtattcaaa tcaca                                                      15
```

```
<210> SEQ ID NO 85
<211> LENGTH: 18
<212> TYPE: DNA
<213> ORGANISM: Homo sapiens

<400> SEQUENCE: 85
cctcgcatcg agataacc                                                 18

<210> SEQ ID NO 86
<211> LENGTH: 18
<212> TYPE: DNA
<213> ORGANISM: Homo sapiens

<400> SEQUENCE: 86
ccaagtattc aaatcaca                                                 18

<210> SEQ ID NO 87
<211> LENGTH: 21
<212> TYPE: DNA
<213> ORGANISM: Homo sapiens

<400> SEQUENCE: 87
agtcctcgca tcgagataac c                                             21

<210> SEQ ID NO 88
<211> LENGTH: 21
<212> TYPE: DNA
<213> ORGANISM: Homo sapiens

<400> SEQUENCE: 88
tgcccaagta ttcaaatcac a                                             21

<210> SEQ ID NO 89
<211> LENGTH: 24
<212> TYPE: DNA
<213> ORGANISM: Homo sapiens

<400> SEQUENCE: 89
agccctcgga tcgagatcac tccg                                          24

<210> SEQ ID NO 90
<211> LENGTH: 24
<212> TYPE: DNA
<213> ORGANISM: Homo sapiens

<400> SEQUENCE: 90
tgcccaagta ttcaaatcac atcc                                          24

<210> SEQ ID NO 91
<211> LENGTH: 27
<212> TYPE: DNA
<213> ORGANISM: Homo sapiens

<400> SEQUENCE: 91
agccctcgga tcgagatcac tccgtcc                                       27

<210> SEQ ID NO 92
<211> LENGTH: 27
<212> TYPE: DNA
<213> ORGANISM: Homo sapiens

<400> SEQUENCE: 92
tgcccaagta ttcaaatcac atccatt                                       27
```

```
<210> SEQ ID NO 93
<211> LENGTH: 9
<212> TYPE: PRT
<213> ORGANISM: Influenza virus

<400> SEQUENCE: 93

Tyr Pro Tyr Asp Val Pro Asp Tyr Ala
1               5

<210> SEQ ID NO 94
<211> LENGTH: 12
<212> TYPE: PRT
<213> ORGANISM: Mus musculus

<400> SEQUENCE: 94

Phe Gln Asn Ile Pro Ala His Tyr Ser Pro Arg Thr
1               5                   10

<210> SEQ ID NO 95
<211> LENGTH: 12
<212> TYPE: PRT
<213> ORGANISM: Mus musculus

<400> SEQUENCE: 95

Pro Ala His Tyr Ser Pro Arg Thr Ser Pro Ile Met
1               5                   10

<210> SEQ ID NO 96
<211> LENGTH: 12
<212> TYPE: PRT
<213> ORGANISM: Mus musculus

<400> SEQUENCE: 96

Ser Pro Arg Thr Ser Pro Ile Met Ser Pro Arg Thr
1               5                   10

<210> SEQ ID NO 97
<211> LENGTH: 20
<212> TYPE: PRT
<213> ORGANISM: Mus musculus

<400> SEQUENCE: 97

Phe Gln Asn Ile Pro Ala His Tyr Ser Pro Arg Thr Ser Pro Ile Met
1               5                   10                  15

Ser Pro Arg Thr
            20

<210> SEQ ID NO 98
<211> LENGTH: 12
<212> TYPE: PRT
<213> ORGANISM: Mus musculus

<400> SEQUENCE: 98

Pro Val Pro Arg Pro Ala Ser Arg Ser Ser Ser Pro
1               5                   10

<210> SEQ ID NO 99
<211> LENGTH: 10
<212> TYPE: PRT
<213> ORGANISM: Mus musculus

<400> SEQUENCE: 99

Arg Pro Ala Ser Arg Ser Ser Ser Pro Gly
1               5                   10
```

<210> SEQ ID NO 100
<211> LENGTH: 12
<212> TYPE: PRT
<213> ORGANISM: Mus musculus

<400> SEQUENCE: 100

Ala Ser Arg Ser Ser Ser Pro Gly Ala Lys Arg Arg
1               5                   10

<210> SEQ ID NO 101
<211> LENGTH: 17
<212> TYPE: PRT
<213> ORGANISM: Mus musculus

<400> SEQUENCE: 101

Pro Val Pro Arg Pro Ala Ser Arg Ser Ser Ser Pro Gly Ala Lys Arg
1               5                   10                  15

Arg

<210> SEQ ID NO 102
<211> LENGTH: 22
<212> TYPE: PRT
<213> ORGANISM: Artificial Sequence
<220> FEATURE:
<223> OTHER INFORMATION: Synthetically generated peptide containing the
      SPRIEITPS amino acid sequence

<400> SEQUENCE: 102

Lys Pro Ala Gly Ala Ser Gly Pro Ser Pro Arg Ile Glu Ile Thr Pro
1               5                   10                  15

Ser His Glu Ala Tyr Asp
            20

<210> SEQ ID NO 103
<211> LENGTH: 17
<212> TYPE: PRT
<213> ORGANISM: Artificial Sequence
<220> FEATURE:
<223> OTHER INFORMATION: Synthetically generated peptide containing the
      SPAIAIAPS amino acid sequence

<400> SEQUENCE: 103

Ser Gly Pro Ser Pro Ala Ile Ala Ile Ala Pro Ser His Glu Ala Tyr
1               5                   10                  15

Asp

<210> SEQ ID NO 104
<211> LENGTH: 4
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 2
<223> OTHER INFORMATION: Xaa = Glu, Arg, or Gln
<220> FEATURE:
<221> NAME/KEY: VARIANT
<222> LOCATION: 3
<223> OTHER INFORMATION: Xaa = Ile, or Phe

<400> SEQUENCE: 104

Ile Xaa Xaa Thr
1

```
<210> SEQ ID NO 105
<211> LENGTH: 4
<212> TYPE: PRT
<213> ORGANISM: Homo sapiens

<400> SEQUENCE: 105

Ile Glu Ile Thr
 1

<210> SEQ ID NO 106
<211> LENGTH: 4
<212> TYPE: PRT
<213> ORGANISM: Homo sapiens

<400> SEQUENCE: 106

Ile Arg Ile Thr
 1

<210> SEQ ID NO 107
<211> LENGTH: 4
<212> TYPE: PRT
<213> ORGANISM: Homo sapiens

<400> SEQUENCE: 107

Ile Gln Ile Thr
 1

<210> SEQ ID NO 108
<211> LENGTH: 4
<212> TYPE: PRT
<213> ORGANISM: Mus musculus

<400> SEQUENCE: 108

Ile Gln Phe Thr
 1

<210> SEQ ID NO 109
<211> LENGTH: 12
<212> TYPE: DNA
<213> ORGANISM: Homo sapiens

<400> SEQUENCE: 109
atcgagatca ct                                                          12

<210> SEQ ID NO 110
<211> LENGTH: 12
<212> TYPE: DNA
<213> ORGANISM: Homo sapiens

<400> SEQUENCE: 110
atcgagataa cc                                                          12

<210> SEQ ID NO 111
<211> LENGTH: 12
<212> TYPE: DNA
<213> ORGANISM: Homo sapiens

<400> SEQUENCE: 111
atccgcatca cc                                                          12

<210> SEQ ID NO 112
<211> LENGTH: 12
<212> TYPE: DNA
<213> ORGANISM: Homo sapiens
```

-continued

```
<400> SEQUENCE: 112
attcaaatta ca                                                            12

<210> SEQ ID NO 113
<211> LENGTH: 12
<212> TYPE: DNA
<213> ORGANISM: Homo sapiens

<400> SEQUENCE: 113
attcaaatca ca                                                            12

<210> SEQ ID NO 114
<211> LENGTH: 12
<212> TYPE: DNA
<213> ORGANISM: Mus musculus

<400> SEQUENCE: 114
atccaattta ca                                                            12
```